(12) United States Patent
Bielec et al.

(10) Patent No.: US 12,296,031 B2
(45) Date of Patent: *May 13, 2025

(54) ESTHETIC DENTAL FILLING MATERIAL WITH HIGH DEPTH OF CURE

(71) Applicant: Ivoclar Vivadent AG, Schaan (LI)

(72) Inventors: Philipp Bielec, Wasserburg (DE); Benjamin Gebhardt, Grabs (CH)

(73) Assignee: Ivoclar Vivadent AG, Schaan (LI)

( * ) Notice: Subject to any disclaimer, the term of this patent is extended or adjusted under 35 U.S.C. 154(b) by 354 days.

This patent is subject to a terminal disclaimer.

(21) Appl. No.: 17/814,392

(22) Filed: Jul. 22, 2022

(65) Prior Publication Data
US 2023/0052305 A1  Feb. 16, 2023

(30) Foreign Application Priority Data
Jul. 27, 2021  (EP) .................................... 21188081

(51) Int. Cl.
| | | |
|---|---|---|
| A61K 6/893 | (2020.01) | |
| A61K 6/16 | (2020.01) | |
| A61K 6/20 | (2020.01) | |
| A61K 6/30 | (2020.01) | |
| A61K 6/77 | (2020.01) | |

(52) U.S. Cl.
CPC ................ *A61K 6/893* (2020.01); *A61K 6/30* (2020.01); *A61K 6/77* (2020.01); *A61K 6/16* (2020.01); *A61K 6/20* (2020.01)

(58) Field of Classification Search
CPC ...................................................... A61K 6/887
See application file for complete search history.

(56) References Cited

U.S. PATENT DOCUMENTS

| | | |
|---|---|---|
| 4,291,047 A | 9/1981 | Kranz et al. |
| 4,447,520 A | 5/1984 | Henne et al. |
| 4,629,746 A | 12/1986 | Michl et al. |
| 4,737,593 A | 4/1988 | Ellrich et al. |
| 5,534,559 A | 7/1996 | Leppard et al. |
| 7,091,258 B2 | 8/2006 | Neubert et al. |
| 8,617,306 B2 | 12/2013 | Lambert et al. |
| 9,833,388 B2 | 12/2017 | Willner et al. |
| 10,322,070 B2 | 6/2019 | Moszner et al. |
| 10,342,744 B2 | 7/2019 | Moszner et al. |

(Continued)

FOREIGN PATENT DOCUMENTS

| | | |
|---|---|---|
| EP | 0934926 A1 | 8/1999 |
| EP | 3854374 A1 | 7/2021 |
| WO | 2017/149242 A1 | 9/2017 |

*Primary Examiner* — Michael F Pepitone
(74) *Attorney, Agent, or Firm* — Ann M. Knab; Thad McMurray

(57) ABSTRACT

A dental material having (a) at least one radically polymerizable monomer, (b) at least one radiopaque filler, (c) at least one inorganic filler, (d) at least one composite filler, and (e) at least one initiator for the radical polymerization, wherein the monomer (a) comprises at least one urethane (meth) acrylate, at least one radically polymerizable bisphenol A derivative, optionally at least one polycyclic aliphatic dimethacrylate, optionally at least one monomer which does not fall into one of the groups (a-1) to (a-3) and (a-5), and optionally at least one chain regulator (a-5). The dental material allows the fabrication of esthetically pleasing restorations with only one material.

16 Claims, 3 Drawing Sheets

(56) References Cited

U.S. PATENT DOCUMENTS

| | | |
|---|---|---|
| 10,555,877 B2 | 2/2020 | Vogel et al. |
| 10,828,240 B2 | 11/2020 | Fukudome et al. |
| 2002/0152930 A1* | 10/2002 | Neubert ................. A61K 31/04 |
| | | 106/35 |
| 2008/0076847 A1 | 3/2008 | Moszner et al. |
| 2010/0035214 A1 | 2/2010 | Reynaud et al. |
| 2017/0224591 A1* | 8/2017 | Vogel ....................... A61K 6/78 |
| 2020/0165363 A1 | 5/2020 | Gebhardt et al. |

* cited by examiner

ESTHETIC DENTAL FILLING MATERIAL WITH HIGH DEPTH OF CURE

CROSS-REFERENCE TO RELATED APPLICATIONS

This application claims priority to European Patent Application No. 21188081.0 filed on Jul. 27, 2021, the disclosure of which is incorporated herein by reference in its entirety.

TECHNICAL FIELD

The present invention relates to radiopaque dental materials which are characterized by a large depth of cure and allow simplified fabrication of esthetically pleasing dental restorations. The materials are particularly suitable as dental filling materials.

BACKGROUND

Methacrylate-based dental filling materials are often referred to as resin fillings or more correctly as composites. Composite materials contain a polymerizable organic matrix and fillers as well as various additives, such as stabilizers, initiators and pigments. The filler content depends largely on the desired intended use and can be up to 90% by weight.

The polymerizable organic matrix of dental restorative composites and adhesives is usually based on a mixture of dimethacrylates, often containing the highly viscous Bis-GMA as crosslinker. Bis-GMA results in good mechanical properties with comparatively low volume shrinkage. Other examples of frequently used dimethacrylates are urethane dimethacrylates and the low-viscosity dimethacrylates bis (methacryloyloxymethyl)tricyclo[5.2.1.]decane (TCDMA), decanediol-1,10-dimethacrylate ($D_3MA$) and triethylene glycol dimethacrylate (TEGDMA), which are regularly used as diluent monomers.

The polymerizable organic matrix usually contains an initiator for free-radical polymerization, and light-curing materials containing a photoinitiator now occupy a dominant position in dental restorative therapy. One disadvantage of light-curing materials is that the placement of large fillings in particular is time-consuming because the light required for curing can penetrate the materials only to a limited depth. In the so-called increment technique, the filling is therefore built up from the composite material in layers, with the layers each having a thickness of approx. 2 mm and having to be individually cured.

This disadvantage is overcome by so-called bulk fill materials, which allow curing depths of approx. 4 mm per layer. Usual filling materials have a depth of cure of about 2 mm. However, bulk-fill materials often do not have the desired esthetic properties and are therefore not suitable or only suitable to a limited extent for anterior restorations. The depth of cure correlates with the translucence of the materials. High translucence and good depth of cure are achieved when the organic matrix and the fillers used have matching refractive indices. The disadvantage here is that, due to their high translucence, such composites only poorly cover the underlying dentin, which is disturbing for esthetic reasons because the color of the dentin differs from that of the visible enamel.

WO 2016/026915 A1 and corresponding U.S. Ser. No. 10/555,877 B2, which US patent is hereby incorporated by reference in its entirety, disclose radically polymerizable dental materials that combine a high depth of cure with good opacity. The materials are characterized in that the monomer mixture used for their production has a refractive index $n_D$ of 1.50 to 1.70 and that the refractive index of the monomer mixture before curing corresponds to the refractive index of the filler or is at most 0.013 greater, but after curing is at least 0.02 greater than the refractive index of the filler. Before polymerization, the dental materials exhibit a high translucence and thus a large depth of cure. During polymerization, the translucence decreases. The materials may contain radiopaque fillers such as radiopaque glasses or ytterbium fluoride with a particle size of 0.050 to 2.0 μm. The materials are suitable as bulk-fill materials, but are not packable due to their flowability.

U.S. Pat. No. 10,828,240, which US patent is hereby incorporated by reference in its entirety, discloses free-radically polymerizable dental materials containing a free-radically polymerizable monomer, inorganic filler and organic-inorganic filler, which are said to have a high depth of cure. This is said to be achieved by the refractive indices of the fillers being in the range of the refractive index of the monomer, wherein In the examples the refractive index of the monomers is smaller than the refractive index of the fillers.

EP 2 965 741 A1 and U.S. Ser. No. 10/342,744 B2, which US patent is hereby incorporated by reference in its entirety, disclose radically polymerizable dental materials that exhibit a delayed gel point and reduced polymerization shrinkage stress in combination with a homogeneous network architecture, a narrow and low glass transition temperature and improved impact strength while maintaining good mechanical properties. These improvements are achieved by using special chain transfer reagents (chain regulators).

U.S. Pat. No. 4,629,746, which US patent is hereby incorporated by reference in its entirety, discloses micro-filled dental materials containing rare earth metal fluorides such as ytterbium fluoride with a primary particle size of 5 to 700 nm, preferably 50 to 300 nm as radiopaque fillers. In addition to the radiopaque fillers, the materials may contain non-radiopaque fillers such as precipitated or fumed silica. The materials are said to exhibit high radiopacity and good transmission.

EP 1 234 567 A2 and corresponding U.S. Pat. No. 7,091,258 B2, which US patent is hereby incorporated by reference in its entirety, disclose prepolymers with defined particle size distribution containing only a small proportion of fine-grained particles with a size of less than 10 μm. These fillers are said to yield polymerizable compositions with low polymerization shrinkage and good polishability, surface smoothness and abrasion resistance. To increase the radiopacity, the prepolymers may contain radiopaque fillers such as ytterbium fluoride with a particle size of 300 nm.

WO 2017/149242 A1 discloses the preparation of colloidal suspensions of ytterbium fluoride with a particle size of less than 100 nm and their use in the preparation of dental materials.

U.S. Pat. No. 9,833,388 B2, which US patent is hereby incorporated by reference in its entirety, discloses dental materials containing ytterbium fluoride with a particle size between 25 and 120 nm. These are said to be characterized by a low number of artifacts in volume tomography.

EP 2 965 741 A1 and corresponding U.S. Ser. No. 10/342,744 B2, which US patent is hereby incorporated by reference in its entirety, disclose the use of free-radically polymerizable sulfur-containing monomers such as 2-(toluene-4-sulfonylmethyl)acrylic acid lauryl ester as chain regulators to reduce polymerization shrinkage stress (PSS) in dental materials.

According to ISO4049:2019, a radiopaque dental material is defined as a material that has at least the same radiopacity as the element aluminum. In order to be seen well in a radiograph, it is recommended that dental materials have twice the radiopacity of aluminium (200% Al), as the radiopacity of natural enamel is equivalent to approximately 170% Al. To give composite materials the desired radiopacity, radiopaque fillers are added. These are usually glasses containing barium or strontium, which have a relatively high refractive index.

The depth of cure of dental materials correlates positively with the translucence of the materials. In order to polymerize dental materials in a layer thickness of 4 mm in one exposure step, a high translucence is required. A high translucence and thus a high depth of cure are achieved when the refractive index of the organic matrix matches the refractive indices of the fillers used. High translucence has the additional advantage that the filling adapts well to the tooth in terms of color. However, the disadvantage is that high translucence results in low opacity, which is different from that of the natural tooth. In the anterior tooth, this results in unnatural gray/dark-looking fillings, as the dark oral cavity shows through, while in the posterior tooth the translucent dentin is visually disadvantageous. Another problem in the production of radiopaque dental materials with a high depth of cure is the high refractive index of the glass fillers. This severely limits the choice of suitable monomers.

Conventional dental materials are usually optimized for specific applications, so that a large number of different materials is available. To achieve a medically and visually satisfactory treatment outcome, it is usually necessary to combine different materials in a suitable manner. This makes the treatment time-consuming and expensive.

SUMMARY

It is an object of the present invention to provide dental materials which do not have the above-mentioned disadvantages. The dental materials should enable the fabrication of esthetically pleasing and medically satisfactory restorations with only one material. The dental materials should produce restorations that blend well with the natural tooth structure in terms of opacity, translucence and color. In addition, the materials should exhibit high gloss stability and good polishability as well as low surface roughness and be radiopaque.

BRIEF DESCRIPTION OF THE DRAWINGS

The invention is explained in more detail below with reference to figures and examples.

DETAILED DESCRIPTION

Figure 1:
FIG. 1 shows a human molar with a left-sided restoration according to the invention and a right-sided restoration with a commercially available composite material (Omnichroma, Tokuyama Dental).

According to the invention, this object is achieved by dental materials which comprise
(a) at least one radically polymerizable monomer,
(b) at least one radiopaque filler,
(c) at least one inorganic filler,
(d) at least one composite filler and
(e) at least one initiator for the radical polymerization.

It has been found that by a targeted selection of substances known per se, dental materials can be produced which meet the above requirements.

Monomer (a)

Preferred monomers (a) are radically polymerizable, polyfunctional monomers and, in particular, (meth)acrylamides and (meth)acrylates. Monofunctional and polyfunctional methacrylates are particularly preferred, and monofunctional and difunctional methacrylates and mixtures thereof are especially preferred. Further preferred are difunctional hybrid monomers. Hybrid monomers are monomers containing both (meth)acrylamide and (meth)acrylate groups.

Polyfunctional monomers are compounds with two or more, preferably 2 to 4 and in particular 2 radically polymerizable groups.

The monomer (a) may comprise a single monomer or preferably a mixture of different monomers. Particularly preferred according to the invention are dental materials in which component (a) contains a mixture of the following monomers:

(a-1) 20 to 80% by weight, preferably 25 to 55% by weight and most preferably 30 to 50% by weight of at least one urethane (meth)acrylate, (a-2) 8 to 45% by weight, more preferably from 10 to 35% by weight and most preferably from 12 to 35% by weight of at least one radically polymerizable bisphenol A derivative, (a-3) 10 to 50% by weight, more preferably from 15 to 40% by weight and most preferably from 20 to 35% by weight, of at least one polycyclic-aliphatic, preferably tricyclic-aliphatic dimethacrylate, particularly preferably tricyclodecane dimethanol dimethacrylate (TCP), (a-4) 0 up to 20% by weight, more preferably 2 to 20% by weight and most preferably from 4 to 10% by weight of other monomers, i.e. monomers which do not fall into any of the groups (a-1) to (a-3) and (a-5), (a-5) 0 up to 8% by weight, preferably 0.5 to 7% by weight and more preferably 1 to 6% by weight of at least one chain regulator, in each case based on the total mass of component (a).

The monomers (a-1) to (a-5) are preferably each selected from the following substances, with dental materials in which component (a) exclusively contains the monomers mentioned being particularly preferred according to the invention. In all cases, individual monomers or a mixture of several monomers may be used. The term (meth)acrylate stands for acrylate, methacrylate or a mixture thereof, the meaning methacrylate being preferred in all cases.

Preferred urethane (meth)acrylates (a-1) are urethane di(meth)acrylates and in particular urethane dimethacrylates.

Particularly preferred are urethane di(meth)acrylates containing aromatic groups, especially the urethane di(meth)acrylate derivatives of 1,3-bis(1-isocyanato-1-methylethyl)benzene described in EP 0 934 926 A1, with tetramethyl-xylylene diurethane di(meth)acrylate (V380) being especially preferred:

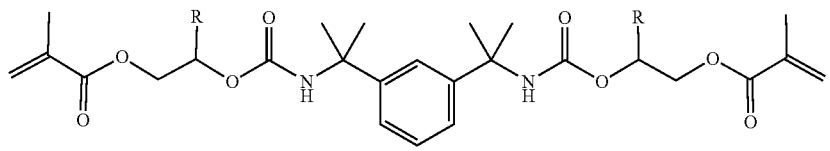

(R = H, CH₃)

In the formula shown, the radicals R are independently H or CH₃, and the radicals may have the same meaning or different meanings. Preferably, a mixture is used containing molecules in which both radicals are H, molecules in which both radicals are CH₃, and molecules in which one radical is H and the other radical is CH₃ (CAS numbers: 17884-94-1 (R=H), 138393-21-2 (R=CH₃), 1219495-43-8 (R=H, CH₃)). Such a mixture is obtainable, for example, by reacting 1,3-bis(1-isocyanato-1-methylethyl)benzene with hydroxypropyl methacrylate and 2-hydroxyethyl methacrylate. Tetramethyl-xylylene diurethane dimethacrylate (R=CH₃) is particularly preferred.

Urethane dimethacrylate monomers containing aromatic groups are preferably used in a total amount of from 5 to 60% by weight, more preferably from 10 to 45% by weight and most preferably from 10 to 25% by weight, based on the mass of monomer component (a).

Further preferred are urethane di(meth)acrylates of the general formula I:

Formula I

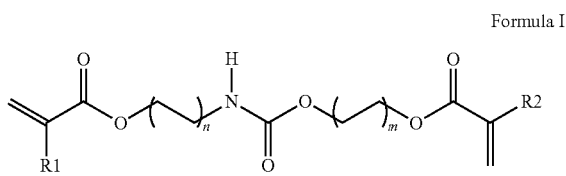

in which the variables have the following meanings:

$R^1$, $R^2$=independently of each other in each case $C_1$-$C_8$-alkyl, preferably $C_1$-$C_4$-alkyl, particularly preferably $C_1$-$C_2$-alkyl, most preferably CH₃; where $R^1$ and $R^2$ are preferably identical, n, m=are each independently an integer from 1 to 2 and preferably 1.

A particularly preferred urethane dimethacrylate of formula I is N-(2-methacryloyloxyethyl)carbamic acid (2-methacryloyloxyethyl) ester (V837; CAS No. 139096-43-8):

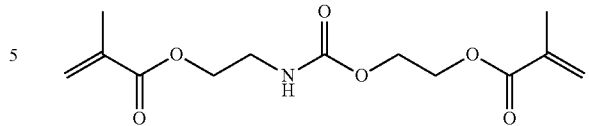

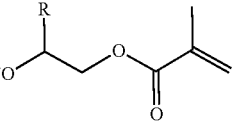

If present, the urethane di(meth)acrylates of formula I are used in an amount of 5% by weight or less, preferably in an amount of 0.01 to 5% by weight, more preferably 0.04 to 4% by weight, based on the mass of monomer component (a).

In addition to the urethane di(meth)acrylates mentioned, the dental materials according to the invention can advantageously contain further urethane di(meth)acrylates, preferably urethane dimethacrylates. These are preferably used in an amount of 10 to 70% by weight, more preferably 15 to 45% by weight and most preferably 15 to 35% by weight, based on the mass of monomer component (a). A particularly preferred urethane dimethacrylate is 7,7(9)9-trimethyl-4,3-dioxo-3,14-dioxa-5,12-diazohexadecane-1,16-diyldimethacrylate (RM3; an addition product of 2-hydroxyethyl methacrylate and 2,2,4-trimethyl hexamethylene diisocyanate).

The preferred component (a-1) is a monomer mixture which contains 5 to 60% by weight, preferably from 10 to 45% by weight and more preferably from 10 to 25% by weight of at least one urethane dimethacrylate monomer having aromatic groups, preferably V380, 0 up to 5% by weight, preferably 0.01 up to 5% by weight and more preferably 0.04 up to 4% by weight of at least one urethane di(meth)acrylate of the formula I, preferably V837 and 10 to 70% by weight, more preferably 15 to 45% by weight and most preferably 15 to 35% by weight of at least one further urethane dimethacrylate, preferably RM3, in each case based on the total mass of the monomer component (a).

The total amount of urethane (meth)acrylates (a-1) is preferably in the range of 20 to 80% by weight, preferably 25 to 55% by weight and more preferably 30 to 50% by weight, based on the mass of monomer component (a).

Preferred radically polymerizable bisphenol A derivatives (a-2) are bisphenol A dimethacrylates, in particular 2,2-bis[4-(2-hydroxy-3-methacryloyloxypropyl)phenyl]propane (bis-GMA) or 2,2-bis(4-methacryloyloxyphenyl)propane (bisphenol A dimethacrylate; CAS no. 3253-39-2), more preferably ethoxylated or propoxylated bisphenol A dimethacrylate and most preferably 2-[4-(2-methacryloyloxyethoxyethoxy)phenyl]-2-[4-(2-methacryloyloxyethoxy)phenyl]propane) (SR-348c, contains 3 ethoxy groups).

The bisphenol A derivative(s) (a-2) is/are preferably used in a total amount of from 8 to 45% by weight, more preferably from 10 to 35% by weight and most preferably from 12 to 35% by weight, based on the mass of the monomer component (a).

Preferred polycyclic aliphatic dimethacrylates (a-3) are cyclic non-aromatic dimethacrylates, wherein the polycyclic aliphatic radical preferably contains 5 to 20 carbon atoms and may optionally contain a heteroatom, particularly preferably contains 5 to 15 carbon atoms and may optionally contain an oxygen, nitrogen or sulfur atom.

Very particularly preferred polycyclic aliphatic dimethacrylates (a-3) are tricyclic dimethacrylates such as tricyclodecane dimethanol dimethacrylate and most preferred the tricyclodecane dimethanol dimethacrylate TCP (CAS number: 42594-17-2). TCP changes its refractive index during polymerization from 1.501 to 1.531.

Polycyclic aliphatic dimethacrylates are preferably used in a total amount of from 10 to 50% by weight, particularly preferably from 15 to 40% by weight and most preferably from 20 to 35% by weight, based on the mass of monomer component (a).

Preferred further monomers (a-4) are (meth)acrylamides, e.g. N-disubstituted (meth)acrylamides, such as N,N-dimethylacrylamide, as well as bis(meth)acrylamides, such as N,N'-diethyl-1,3-bis(acrylamido) propane, 1,3-bis(methacrylamido)propane, 1,4-bis(acrylamido)butane and 1,4-bis(acryloyl)piperazine. More preferred are monofunctional methacrylates as well as polyfunctional, preferably difunctional, methacrylates, such as di-, tri- or tetraethylene glycol dimethacrylate, trimethylolpropane trimethacrylate, pentaerythritol tetramethacrylate, glycerol dimethacrylate and glycerol trimethacrylate, 1,4-butanediol dimethacrylate, 1,10-decanediol dimethacrylate ($D_3MA$), 1,12-dodecanediol dimethacrylate. According to a particularly preferred embodiment, the dental materials according to the invention contain at least one monofunctional methacrylate, more preferably 2-([1,1'-biphenyl]-2-oxy)ethyl methacrylate (MA836), or a mixture of mono- and difunctional methacrylates, in particular a mixture of 2-([1,1'-biphenyl]-2-oxy) ethyl methacrylate (MA836) and 1,10-decanediol dimethacrylate ($D_3MA$).

1,10-Decanediol dimethacrylate ($D_3MA$) and 2-([1,1'-biphenyl]-2-oxy)ethyl methacrylate (MA836) are characterized by a large refractive index difference between monomer and polymer forms (1.460 to 1.500 for D3MA and 1.575 to 1.598 MA-836). $D_3MA$ has a very low refractive index and MA-836 has a very high refractive index. The monomers are therefore particularly suitable for adjusting the refractive index of the monomer component (a).

The compositions according to the invention can further contain one or more so-called hybrid monomers as monomer (a-4). These are monomers which contain at least one (meth)acrylamide and one (meth)acrylate group. Preferred monomers of this type are the hybrid monomers disclosed in EP 3 064 192 A1 and corresponding U.S. Ser. No. 10/322,070 B2, which US patent is hereby incorporated by reference in its entirety, with monomers containing methacrylamide groups and methacrylate groups being particularly preferred. Most preferred are hybrid monomers which additionally comprise a urethane group.

Monomers (a-4) are preferably used in a total amount of not more than 20% by weight, more preferably 2 to 20% by weight and most preferably 4 to 10% by weight, based on the mass of monomer component (a). The total amount of monofunctional radically polymerizable monomers used is preferably 20% by weight or less, more preferably 1 to 17% by weight, very particularly preferably 2 to 14% by weight and most preferably 3 to 11% by weight, based on the monomer component (a). Monofunctional radically polymerizable monomers are more easily washed out of the cured material after polymerization than polyfunctional monomers, which is undesirable from a toxicological point of view. For this reason, dental materials are preferred according to the invention which, based on the total mass of the dental material, contain less than 2% by weight, more preferably 0.1 to 1.9% by weight, very particularly preferably 0.2 to 1.8% by weight and most preferably 1.3 to 1.7% by weight of monofunctional radically polymerizable monomers.

Preferred chain regulators (a-5) are the radically polymerizable, sulfur-containing monomers disclosed in EP 2 965 741 A1 and corresponding U.S. Ser. No. 10/342,744 B2, which US patent is hereby incorporated by reference in its entirety. More preferred chain regulators (a-5) are compounds from the group of allyl sulfones. Particularly suitable allyl sulfones are 2-(toluene-4-sulfonylmethyl)-acrylic acid ethyl ester (TSMEA), 2-(toluene-4-sulfonylmethyl)-acrylic acid 2-(2-ethoxy-ethoxy)-ethyl ester, 2-(toluene-4-sulfonylmethyl)-acrylic acid, 2-(toluene-4-sulfonylmethyl)-acrylic acid tert-butyl ester, 3-(trimethoxysilyl)propyl-2-(tosylmethyl)acrylate, 3-(triethoxysilyl)propyl-2-(tosylmethyl)acrylate, 3-(triethoxysilyl)propyl-2-(tosylmethyl)acrylamide, 2-(methylsulfonyl)ethyl methacrylate, 2-(methylsulfonyl) ethyl methacrylate, 3-(methylsulfonyl)propyl methacrylate, triethylene glycol bis[2-(toluene-4-sulfonylmethyl) acrylate], 2-(toluene-4-sulfonylmethyl) acrylic acid (2-methacryloyloxyethyl) ester, 2-(toluene-4-sulfonylmethyl)acrylic acid (6-methacryloyloxyhexyl) ester, 2-(toluene-4-sulfonylmethyl) acrylic acid (10-methacryloyloxydecyl) ester, 2-(toluene-4-sulfonylmethyl) acrylic acid (2-hydroxy-3-methacryloyloxypropyl) ester, 2-(toluene-4-sulfonylmethyl) acrylic acid (8-meth acryl oyloxy-3,6-dioxaoctyl) ester, with 2-(toluene-4-sulfonylmethyl) acrylic acid ethyl ester (TSMEA) being particularly suitable. Chain regulators are monomers that control chain growth during polymerization. This results in a reduction of the shrinkage force. A low shrinkage force has a beneficial effect on the edge tightness of fillings. Chain regulators are also referred to as chain transfer agents.

Chain regulators are preferably used in an amount of from 0 to 8% by weight, more preferably from 0.5 to 7% by weight and most preferably from 1 to 6% by weight, based on the mass of monomer component (a).

The total amount of radically polymerizable monomers (a) is preferably in a range from 5 to 40% by weight, more preferably from 10 to 35% by weight, very particularly preferably from 12 to 30% by weight, and most preferably from 15 to 25% by weight, based on the total mass of the dental material.

Particularly preferred according to the invention are dental materials containing as component (a-1) tetramethylxylylene diurethane dimethacrylate (V380), 1,6-bis-[2-methacryloyloxy-ethoxycarbonylamino]-2,2,4-trimethylhexane (RM3), N-(2-methacryloyloxyethyl) carbamic acid-(2-methacryloyloxyethyl) ester (V837; CAS no. 139096-43-8) or any mixture thereof; as component (a-2) bisphenol A dimethacrylate, ethoxy- or propoxylated bisphenol A dimethacrylate, in particular bisphenol A dimethacrylate 2-[4-(2-methacryloyloxyethoxyethoxy)phenyl]-2-[4-(2-methacryloyloxyethoxy)phenyl]propane) (SR-348c), 2,2-bis[4-(2-hydroxy-3-methacryloyloxypropyl) phenyl]propane (Bis-GMA) or any mixture thereof; as component (a-3) bis-(3-methacryloyloxymethyl)tricyclo-[5.2.1.$0^{2,6}$]decane (TCP); as component (a-4) 2-([1,1'-biphenyl]-2-oxy)ethyl methacrylate (MA-836) and/or 1,10-decanediol dimethacrylate (D₃MA); and as component (a-5) 2-(toluene-4-sulfonylmethyl) acrylic acid ethylester (MA-769).

The monomer component (a) preferably has a refractive index of 1.495 to 1.520, more preferably 1.505 to 1.515. The refractive index of the monomer mixture is preferably adjusted so that it corresponds to the refractive index of the filler (c) before curing or is at most 0.03 above it. Preferably, the refractive index of the monomer or monomer mixture is 0.002 to 0.02, more preferably 0.005 to 0.015, higher than the refractive index of filler (c). The refractive index of component (a) can be adjusted by mixing monomers with different refractive indices. Due to the small difference in the refractive indices of monomer and filler, the dental materials according to the invention exhibit high translucence before polymerization, so that the light used for polymerization can penetrate deeply into the materials, which ensures a large depth of cure. During polymerization, the refractive index of the monomers increases, while the refractive index of the filler remains unchanged. As a result, the difference between the refractive indices of monomer and filler increases, and the translucence decreases accordingly. This is advantageous for esthetic reasons, because deeper layers of the tooth having a different shade are better covered.

According to the invention, monomers and monomer mixtures are preferred which exhibit a large change in refractive index upon polymerization. The monomers used as component (a) are preferably selected such that the refractive index difference between the unpolymerized and the polymerized state is at least 0.015, preferably at least 0.02. According to a particularly preferred embodiment, the refractive index difference is from 0.015 to 0.04, more preferably from 0.021 to 0.035 and most preferably from 0.022 to 0.030.

X-Ray Opaque Fillers (b)

The materials according to the invention contain as component (b) at least one X-ray opaque filler, preferably tantalum(V) oxide, barium sulfate, a mixed oxide of $SiO_2$ with ytterbium(III) oxide or tantalum(V) oxide, a rare earth fluoride, preferably ytterbium trifluoride, or a mixture thereof, ytterbium trifluoride ($YbF_3$) being particularly preferred.

The X-ray opaque filler(s) (b) are present in particulate form and preferably have a mean particle size of ≤25 nm, preferably <25 nm, more preferably from 10 to 24 nm and most preferably from 15 to 24 nm, the particles being in non-aggregated and non-agglomerated form. Particles with a particle size of ≤25 nm are referred to herein as nanoscale. Quite preferably, the materials according to the invention contain as X-ray opaque filler (b) ytterbium trifluoride particles with an average primary particle size of ≤25 nm, preferably <25 nm, more preferably from 10 to 24 nm very particularly preferably from 15 to 24 nm and most preferably 18 to 22 nm. All particle sizes relating to component (b) are number-averaged values (D50 values, i.e. 50% of the absolute number of particles have a diameter smaller than the specified D50 value).

All other particle sizes are volume-averaged particle sizes (D50 values, i.e. 50% of the total volume of all particles is contained in particles having a diameter smaller than the specified value), unless otherwise stated. Particle size determination in the range from 0.1 μm to 1000 μm is preferably performed by static light scattering (SLS), for example with a LA-960 static laser scattering particle size analyzer (Horiba, Japan) or with a Microtrac S100 particle size analyzer (Microtrac, USA). Here, a laser diode with a wavelength of 655 nm and an LED with a wavelength of 405 nm are used as light sources. The use of two light sources with different wavelengths enables the measurement of the entire particle size distribution of a sample in only one measurement run, whereby the measurement is carried out as a wet measurement. For this purpose, an aqueous dispersion of the filler is prepared and its scattered light is measured in a flow cell. The scattered light analysis for calculating particle size and particle size distribution is carried out according to the Mie theory according to DIN/ISO 13320. The measurement of the particle size in a range from 1 nm to 0.1 μm is preferably carried out by dynamic light scattering (DLS) of aqueous particle dispersions, preferably with a He—Ne laser with a wavelength of 633 nm, at a scattering angle of 90° and at 25° C., e.g. with a Malvern Zetasizer Nano ZS (Malvern Instruments, Malvern UK).

In the case of aggregated and agglomerated particles, the primary particle size can be determined from TEM images. Transmission electron microscopy (TEM) is preferably performed using a Philips CM30 TEM at an accelerating voltage of 300 kV. For sample preparation, drops of the particle dispersion are applied to a 50 Å thick copper grid (mesh size 300 mesh) coated with carbon, followed by evaporation of the solvent. The particles are counted and the arithmetic mean is calculated.

It was found that ytterbium trifluoride particles in particular with a size smaller than 25 nm allow an increase in the radiopacity of the materials, but have only a small effect on the refractive index of the composition. Thus, unlike radiopaque glasses, they do not require the use of monomers with a high refractive index to ensure good translucence. Thus, it is possible to use monomers with low refractive index and large refractive index change.

According to a preferred embodiment, the ytterbium trifluoride particles are surface modified. For this purpose, they are preferably treated with an organic compound having functional groups capable of binding to the surface of the ytterbium trifluoride particles. Preferred functional groups are phosphate, phosphonate, carboxyl, dithiophosphate, and dithiophosphonate groups. Preferably, the surface modifiers also have radically polymerizable groups that enable cross-linking with the organic component (a).

Preferred surface modifiers are P-7,10,13,16-tetraoxaheptadec-1-yl-phosphonic acid, P-[6-[2-[2-(2-hydroxyethoxy)ethoxy]ethoxy]hexyl]phosphonic acid, 2,3-di-(methacryloyloxy)-propyl-1-phosphonic acid, 2,3-di-(methacryloyloxy)-propyl-1-bisphosphonic acid and 3-O-benzyloxy-2-methacryloyloxy-propyl-1-bisphosphonic acid.

The dental materials according to the invention preferably contain 1 to 30% by weight, more preferably 3 to 10% by weight and most preferably 5 to 10% by weight of nanoscale radiopaque fillers, in particular ytterbium trifluoride particles, based on the mass of the dental material.

Inorganic Filler (c)

Preferred inorganic fillers (c) are glass powders, preferably strontium glass powders and/or zirconium-containing glass powders. A particularly preferred glass is the glass with CAS number 65997-17-3. The glass powders preferably have an average particle size of 0.1 to 1.5 μm, more preferably 0.3 to 1.2 μm and very particularly preferably 0.4 to 0.9 μm, most preferably 0.4 to 0.8 μm, for example 0.7 μm. Coarser particles with a size of 1.5 μm to 10 μm, preferably 3 to 9 μm, may optionally be present in a total amount of 0 to 15% by weight, preferably 0 to 10% by weight, based on the total mass of the dental material.

The use of nanoscale ytterbium trifluoride to achieve X-ray opacity makes it possible to dispense with the use of glass powders with a high barium content. These have a relatively high refractive index of 1.53. However, glass powders with a low barium content, preferably of less than 20 wt % (measured as BaO, based on the mass of the glass), can be used. These have a refractive index of about 1.50. Barium-free glass powders are particularly preferred.

Further preferred according to the invention are glasses with a refractive index below 1.525, more preferably below 1.520 and most preferably below 1.515. Preferably, the refractive index of the glasses is in a range of 1.490 to 1.525, more preferably 1.490 to 1.520 and most preferably 1.49 to 1.515. When these glasses are combined with appropriate monomer mixtures, they surprisingly give particularly good depths of cure.

Inorganic glasses are preferably used in an amount of 20 to 80% by weight, more preferably 25 to 70% by weight, and most preferably 30 to 60% by weight, based on the total mass of the dental material.

Other preferred inorganic fillers (c) are $SiO_2/ZrO_2$ mixed oxides, for example with a volume-average primary particle size of 2 to 100 nm, preferably 2 to 60 nm, more preferably 2 to 40 nm and most preferably 3 to 30 nm. The primary particles are spherical and aggregated to secondary particles with a size of 0.5 to 30 µm, preferably 2 to 25 µm, more preferably from 3 to 20 µm and most preferably 3 to 15 µm. They can be produced according to U.S. Pat. No. 8,617,306 B2.

The addition of the $SiO_2/ZrO_2$ mixed oxide can improve the polishability of the compositions according to the invention. Preferred are $SiO_2/ZrO_2$ mixed oxides with a refractive index in a range of 1.490 to 1.525, more preferred 1.490 to 1.520 and most preferred 1.49 to 1.515. The $SiO_2/ZrO_2$ mixed oxide(s) are preferably added in an amount of 1 to 30 wt. %, more preferably 2 to 20 wt. % and most preferably 5 to 15 wt. %, for example in an amount of 10 wt. %, based on the total mass of the dental material. Preferred are mixed oxides containing 23 wt. % or less $ZrO_2$, more preferred 1 to 20 wt. % $ZrO_2$ and most preferred 5 to 18 wt. % $ZrO_2$.

According to the invention, dental materials are particularly preferred which contain as filler (c) a mixture of at least one glass powder and at least one $SiO_2/ZrO_2$ mixed oxide.

To achieve a high depth of cure of the dental materials according to the invention, the refractive indices of the filler (c) and the monomer component (a) are preferably matched to each other as described above. Preferably, the monomer component (a) is adjusted to a refractive index which is identical to the refractive index of the filler (c), or at most 0.03 higher. Particularly preferably, the refractive index of monomer component (a) is 0.002 to 0.02, and most preferably 0.005 to 0.015, greater than the refractive index of filler (c).

The materials according to the invention can contain a filler or a filler mixture as filler (c). When using filler mixtures, preference is given to materials which contain as component (c) predominantly, i.e. more than 50% by weight, preferably more than 70% by weight, more preferably more than 80% by weight, based on the total mass of component (c), most preferably exclusively such fillers whose refractive index lies in the above-mentioned range.

The refractive index is a material-specific characteristic value that depends on the wavelength of the light used, the temperature, the pressure and the purity of the material. Unless otherwise stated, the term refractive index is used here in all cases to mean the refractive index (no) measured at room temperature with standard light D65. The refractive index of liquid monomers and monomer mixtures can be determined using a commercially available Abbe refractometer.

The refractive index (RI) of solid substances, such as inorganic fillers or composite fillers, is determined by the immersion method. The substances are dispersed at room temperature (23° C.) in mixtures of liquids with different refractive indices (so-called immersion liquids). The greater the difference in refractive index between the liquid and the solid, the more clearly the contours of the solid particles appear. If the refractive index of the liquid is altered so that it approaches that of the solid, the particle contours become weaker and disappear completely when the refractive indices are equalized. Liquids with a known refractive index are suitable as immersion liquids, e.g. mixtures of benzyl salicylate ($n_D^{20}$=1.536) and triacetin ($n_D^{20}$=1.431) or bromonaphthalene ($n_D^{20}$=1.657). By varying the proportions of these substances, the refractive index of the mixture can be matched to that of the solid being measured. If the refractive indices match, the refractive index of the immersion liquid is determined with a refractometer.

To improve the bond between the filler particles and the polymerization matrix, the fillers are preferably surface modified, especially preferably by silanization, more preferably with radically polymerizable silanes, in particular with 3-methacryloyloxypropyltrimethoxysilane. For surface modification of non-silicate fillers, e.g. of $ZrO_2$ or $TiO_2$, functionalized acid phosphates, such as 10-methacryloyloxydecyl dihydrogen phosphate, can also be used.

Composite Filler (d)

The materials according to the invention contain at least one composite filler as component (d). Composite fillers are agglomerates consisting of inorganic fillers bonded together by a polymer matrix. Agglomeration of the fine inorganic filler particles to form composite fillers with an average particle size of 5 to 100 µm, more preferably 10 to 60 µm and most preferably 15 to 40 µm, reduces the surface area of the filler particles to be wetted by the radically polymerizable monomer (a), which lowers the monomer content and thus has a positive effect, for example, on the volume shrinkage and thus the marginal quality of the dental material.

In the case of the composite fillers, the refractive index of the cured polymer matrix is preferably chosen to match the refractive index of the inorganic filler contained therein or differs from it by at most of ±0.2, preferably at most of ±0.1, and more preferably at most ±0.01, so that the particles of the composite filler exhibit high translucence. If more than one inorganic filler is used for the preparation of the composite filler, preferably the predominant amount of the inorganic fillers, i.e. more than 50% by weight, more preferably more than 80% by weight based on the mass of the inorganic fillers, has a refractive index in the above-mentioned range.

The composite fillers are preferably prepared by curing composite pastes containing one or more radically polymerizable monomers and one or more inorganic fillers. For the preparation of composite fillers, the monomers mentioned as component (a), the fillers mentioned as components (b) and (c) and the initiators mentioned as component (e) are preferred. Such mixtures of components (a), (b), (c) and (e) for the preparation of composite fillers are also subject of the invention.

Particularly preferred radically polymerizable monomers for the preparation of the composite fillers are di(meth) acrylates, more preferably glycerol dimethacrylate (GDMA, RI=1.477), alkylene dimethacrylates, most preferably 1,10-decanediol dimethacrylate ($D_3MA$, RI=1.460) and triethylene glycol dimethacrylate (TEGDMA, RI=1.461), as well as urethane dimethacrylates, more preferably RM3 and V837, and most preferably urethane dimethacrylates with aromatic groups, especially V380, and mixtures thereof. Most preferred are D$_3$MA, V380, RM3 and mixtures thereof.

1,10-decanediol dimethacrylate is characterized by a particularly low refractive index (RI). The urethane dimethacrylate RM3, with a refractive index of 1.485, is also among the low-refractive monomers. V380, with 1.513, has a significantly lower refractive index than Bis-GMA with 1.552, but has its good mechanical effect on the composite.

Preferred fillers for the preparation of the composite filler are glasses with a refractive index below 1.525, more preferably below 1.520 and most preferably below 1.515. Preferably, the refractive index of the glasses is in a range from 1.490 to 1.525, more preferably 1.490 to 1.520 and most preferably 1.49 to 1.515. Particularly preferred are strontium glasses, barium-containing glasses, preferably with a BaO content of less than 20% by weight (measured as BaO, based on the mass of the glass), and/or zirconium-containing glass fillers. Strontium glass fillers are particularly preferred. The glass fillers preferably have a particle size of 0.4 to 1 μm, with strontium glass powders having a particle size of 0.4 to 1 μm being particularly preferred. Other particularly preferred inorganic fillers are the SiO$_2$/ZrO$_2$ mixed oxides defined above.

For the preparation of the composite filler (d), inorganic fillers (c) are preferably used which have a refractive index in a range from 1.490 to 1.525, more preferably 1.490 to 1.520 and most preferably 1.49 to 1.515.

According to the invention, composite fillers containing ytterbium trifluoride as inorganic filler are particularly preferred, with the nanoscale ytterbium trifluoride used as component (b) being preferred. Very particularly preferred are ytterbium trifluoride particles with a number-average particle size (D50 value) of <25 nm. The composite filler preferably contains 1 to 20% by weight, more preferably 8 to 13% by weight, of ytterbium trifluoride particles, based on the total mass of the composite filler.

Advantageously, the composite filler may also contain a mixture of said glasses, mixed oxides and/or ytterbium trifluoride, particularly preferably a mixture of ytterbium trifluoride with at least one SiO$_2$/ZrO$_2$ mixed oxide.

Preferred according to the invention are composite fillers obtainable by polymerization of the following composition:
  8 to 50% by weight, preferably 18 to 50% by weight, of radically polymerizable monomer,
  1 to 20 wt %, preferably 8 to 13 wt % ytterbium trifluoride particles, preferably with an average particle size (number-averaged D50 value) of <25 nm,
  40 to 90% by weight, preferably 50 to 70% by weight, of further inorganic fillers, preferably SiO$_2$/ZrO$_2$ mixed oxide and
  0.01 to 2% by weight, preferably 0.1 to 1% by weight, of initiator for the radical polymerization.

All percentages refer to the total mass of the composite filler unless explicitly stated otherwise.

The compositions can be ground after polymerization and used as powder. Polymerization is preferably thermal or photochemical. Ground particles usually have a splinter-like shape. The ground composite fillers preferably have an average particle size of from 10 to 50 μm, more preferably from 10 to 40 μm and most preferably from 30 to 40 μm. They preferably contain a maximum of 10% by weight, based on the mass of the ground composite filler, of particles with a mean size of <10 μm. Preferred composite fillers of this type and methods for their production are described in EP 1 234 567 A2 and corresponding U.S. Pat. No. 7,091,258 B2, which US patent is hereby incorporated by reference in its entirety.

The known peroxides such as dibenzoyl peroxide, dilauroyl peroxide, tert-butyl peroctoate or tert-butyl perbenzoate can be used as initiators for thermal polymerization, but α,α'-azobis(isobutyroethylester), benzpinacol and 2,2'-dimethyl benzpinacol are also suitable. Preferred thermal initiators are described as in EP 1 234 567 A2.

Figure 5:
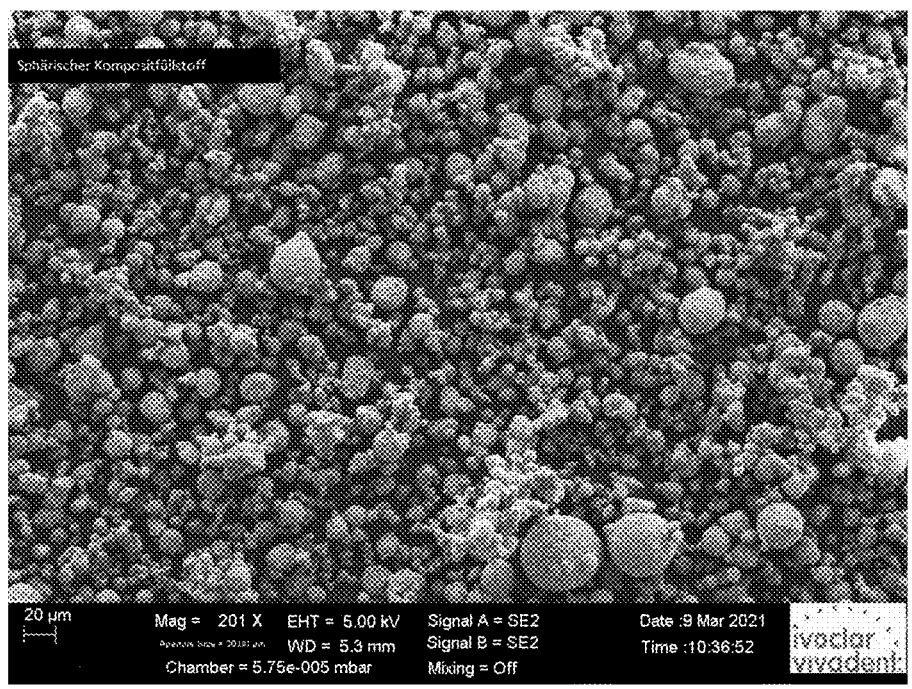
FIG. 5 shows a scanning electron micrograph of the spherical particles of Example 1 at 200× magnification.

According to a particularly preferred embodiment, the particles of the composite filler have a spherical or spheroidal shape (compare FIG. 5). These particles can be produced, for example, by so-called inflight polymerization (aerosol polymerization). For this purpose, the unpolymerized starting material for producing the composite filler is sprayed in the form of small droplets into a polymerization chamber and is then polymerized by irradiation with light of a suitable wavelength, preferably in the blue range. If necessary, the polymerizable mixture can be diluted with a suitable solvent before spraying to adjust the particle size. The solvent evaporates during spraying and does not affect the composition of the filler.

Suitable initiators for light curing are the photoinitiators mentioned as component (e), especially 4,4'-dichlorobenzil or its derivatives as well as camphorquinone, preferably in combination with an amine as accelerator, such as ethyl 4-(dimethylamino)-benzoate, and dibenzoyl germanium derivatives such as bis-(4-methoxybenzoyl)diethylgermanium.

Spherical composite fillers may also contain the above-mentioned substances as inorganic fillers, whereby strontium glass fillers, ytterbium trifluoride, preferably nanoscale ytterbium trifluoride, and/or especially the SiO$_2$/ZrO$_2$ mixed oxides defined above are preferred here. A mixture of nanoscale ytterbium trifluoride and SiO$_2$/ZrO$_2$ mixed oxide is most preferred. The strontium glass powder preferably has a particle size in the range of 0.4 to 1 μm, more preferably 0.5 to 0.8 μm.

The polymerized, spherical or spheroidal composite filler preferably has an average particle size of 5 to 100 μm, more preferably 10 to 60 μm and most preferably 15 to 40 μm.

The refractive indices of the filler (d) and the monomer component (a) are preferably matched to each other such that the refractive index of component (a) corresponds to the refractive index of filler (d) or is at most 0.025 greater. Preferably, the refractive index of monomer component (a) is at most up to 0.02, particularly preferably at most up to 0.01, greater than the refractive index of the filler (d).

The materials according to the invention may contain a filler or a filler mixture as filler (d). When using filler mixtures, materials are preferred which contain as component (d) predominantly, i.e. more than 50% by weight, more preferably more than 80% by weight, in each case based on the total mass of component (d), most preferably exclusively such composite fillers whose refractive indices meet the above condition.

Composite fillers (d) are preferably used in an amount of 5 to 60% by weight, more preferably 15 to 50% by weight and most preferably 15 to 40% by weight, based on the total mass of the dental material.

Initiator for Radical Polymerization (e)

The materials according to the invention contain as component (e) at least one initiator for the radical polymerization, preferably a photoinitiator.

Preferred photoinitiators are photosensitizers, especially α-diketones, such as 9,10-phenanthrenequinone, 1-phenyl-propane-1,2-dione, diacetyl or 4,4'-dichlorobenzil or their derivatives, more preferably camphorquinone (CC) and its derivatives, and mixtures thereof.

The photoinitiators are preferably used in combination with accelerators. Particularly suitable accelerators are tertiary amines, such as tertiary aromatic amines, especially N,N-dialkyl-anilines, -p-toluidines or -3,5-xylidines, p-(N, N-dialkylamino-phenylethanol, -benzoic acid derivatives, -benzaldehyde, -phenyl acetic acid esters and -phenylpropionic acid esters. Specific examples are N,N-dimethyl aniline, N,N-dimethyl-p-toluidine, N,N,3,5-tetramethylaniline, N,N-dimethylamino-p-benzaldehyde, p-(dimethylamino)-benzoic acid ethyl ester or p-(dimethylamino)-benzonitrile. Also suitable are tertiary aliphatic amines, such as tri-n-butylamine, dimethylaminoethan-2-ol, triethanolamine, dimethylaminoethyl methacrylate, N,N-dimethylbenzylamine, or heterocyclic amines, such as 1,2,2,6,6-pentamethylpiperidine, and amino acid derivatives, such as N-phenylglycine. Alternatively, amine-free accelerators can be used, such as sulfinic acids and sulfinates, borates, enolates, phosphines, or other compounds containing active hydrogen atoms, e.g. heterocyclic compounds such as morpholine derivatives or 1,3-dioxolanes.

Other photoinitiators preferred according to the invention are acyl or bisacyl phosphine oxides, in particular the initiators described in EP 0 007 505 A2 and corresponding U.S. Pat. No. 4,291,047A, which US patent is hereby incorporated by reference in its entirety, EP 0 073 413 A2 and corresponding U.S. Pat. No. 4,447,520 A, which US patent is hereby incorporated by reference in its entirety, EP 0 184 095 A2 and corresponding U.S. Pat. Nos. 4,737,593 A and 4,792,632 A, which US patents are hereby incorporated by reference in their entirety, and EP 0 615 980 A2 and corresponding U.S. Pat. No. 5,534,559 A, which US patent is hereby incorporated by reference in its entirety. Preferred examples are the commercially available compounds 2,4,6-trimethylbenzoyldiphenylphosphine oxide (Lucirin™ TPO, BASF) and bis(2,4,6-trimethylbenzoyl)phenylphosphine oxide (Irgacure™ 819, Ciba). Acyl and bisacyl phosphine oxides belong to the group of monomolecular photoinitiators and are characterized by low inherent absorption. Acyl and bisacylphosphine oxides can have a detrimental effect on depth of cure and Vickers hardness at depth and are therefore preferably used in an amount of less than 0.03% by weight, more preferably 0.01% by weight or less. In a very preferred embodiment, no acyl or bisacyl phosphine oxides are used.

Particularly preferred photoinitiators are acyl or bisacylgermanium compounds, especially the monoacyltrialkyl and bisacyldialkylgermanium compounds disclosed in EP 1 905 413 A1 and corresponding US 2008076847 A1, which US publication is hereby incorporated by reference in its entirety, such as benzoyltrimethylgermanium, bisbenzoyldiethylgermanium or bis(4-methoxybenzoyl)-diethylgermanium. Acyl- and bisacylgermanium compounds have the advantage that they decolorize after irradiation (bleaching effect) and thus do not impair the transmission of the cured materials. Moreover, they are monomolecular photoinitiators, i.e. they do not require an accelerator to achieve their full activity.

Photoinitiators can be monomolecular (Norrish type 1) or bimolecular (Norrish type 1l). According to the invention, a combination of at least one monomolecular and at least one bimolecular photoinitiator is preferably used. Such combinations are described, for example, in EP 3 659 575 A1 and corresponding US 2020165363 A1, which US publication is hereby incorporated by reference in its entirety. Particularly preferably, the at least one monomolecular photoinitiator and the at least one bimolecular photoinitiator are used in a ratio of 1.4:1 to 1:2, based on their weight fractions.

Preferred monomolecular photoinitiators are monoacyl or bisacylphosphine oxides, diacyldialkylgermanium and tetraacylgermanium compounds, and tetraacylstannanes. Particularly preferred monomolecular photoinitiators are 2,4,6-trimethylbenzoyldiphenylphosphine oxide, bis(2,4,6-trimethylbenzoyl)phenylphosphine oxide, dibenzoyldiethylgerman, bis(4-methoxybenzoyl)diethylgerman (MBDEGe, Ivocerin®), tetrabenzoylgerman, tetrakis (o-methylbenzoyl)german, tetrakis(mesitoyl)stannane and mixtures thereof.

Preferred bimolecular photoinitiators are α-diketones or derivatives thereof. Particularly suitable α-diketones or derivatives thereof are camphorquinone (CQ), 9,10-phenanthrene quinone, 1-phenyl-propane-1,2-dione, 2,2-dimethoxy-2-phenyl-acetophenone, diacetyl or 4,4'-dichlorobenzil or derivatives thereof. Most preferred are camphorquinone (CQ), 2,2-dimethoxy-2-phenyl-acetophenone and mixtures thereof. Most preferred are α-diketones in combination with amines as reducing agents, such as 4-(dimethylamino)-benzoic acid ester (EDMAB), N,N-dimethylaminoethyl methacrylate, N,N-dimethyl-sym.-xylidine, triethanolamine and mixtures thereof. Preferably, a ratio of bimolecular photoinitiator to amine of 1:1 to 1:6, based on their weight fractions, is used.

Particularly preferred combinations of at least one monomolecular photoinitiator, at least one bimolecular photoinitiator and at least one amine as reducing agent are mixtures containing as monomolecular photoinitiator bis(4-methoxybenzoyl)diethylgerman (MBDEGe, Ivocerin®), bis(2,4,6-trimethylbenzoyl)phenylphosphine oxide, tetrakis(o-methylbenzoyl)german, tetrakis(mesitoyl)stannane or any mixture thereof, camphorquinone (CQ) and/or 2,2-dimethoxy-2-phenyl-acetophenone as bimolecular photoinitiator and 4-(dimethyl-amino)benzoic acid ester (EDMAB) as reducing agent. Most preferably, a mixture of bis(4-methoxybenzoyl)diethylgerman (MBDEGe, Ivocerin®) and camphorquinone and 4-(dimethyl-amino) benzoic acid ester (EDMAB) is used.

Initiators are preferably used in an amount of 0.005 to 3.0% by weight, particularly preferably 0.01 to 2.0% by weight, especially preferably 0.1 to 1% by weight, based on the total mass of the dental material. These quantities include all initiator components, such as accelerators.

Compositions according to the invention containing one of said initiators can be cured, for example, by irradiation with blue light (wavelength range from 400 to 500 nm), preferably by irradiation with an LED lamp having a power between 1200±120 mW/cm$^2$ and 3050±305 mW/cm$^2$.

Colorant

The materials according to the invention are preferably colored with dyes and/or color pigments. According to the 16 colors of the VITA classical A1-D4@ shade guide, natural teeth can be divided into four groups (reddish-brownish, reddish-yellowish, grayish, reddish-gray). To achieve a natural shade, red, yellow, black and/or white dyes and/or pigments are preferably combined, whereby one or more dyes and/or pigments can be used per shade.

Pigments preferred according to the invention are inorganic pigments, such as oxides, oxide hydrates, particularly preferred are metal oxide, semi-metal oxide and metal oxide hydrate pigments. Most preferred pigments are the oxides of the elements iron, titanium and silicon, and the oxide hydrates of the element iron.

Preferred organic dyes are dyes containing at least one cyclic aromatic $C_6$ unit and azo dyes. Particularly preferred are azo dyes containing at least one cyclic aromatic $C_6$ unit.

According to the invention, preferably at least 3, more preferably 3 to 10, very particularly preferably, 3 to 9 and most preferably 3 to 7 different color pigments and/or dyes are used, which according to a particularly preferred embodiment are selected from the above-mentioned dyes and pigments, preferably pigments.

Other Components

The compositions according to the invention can also contain further additives, in particular rheology modifiers, stabilizers, such as polymerization stabilizers, antibacterial agents, fluoride ion-releasing additives, optical brighteners, fluorescent agents, UV absorbers, substances for improving fracture toughness and/or effect agents. The total amount of additives is preferably at most 4% by weight, more preferably at most of 3% by weight, based on the total mass of the material.

The dental materials according to the invention preferably contain:
- 5 to 40% by weight, preferably 10 to 35% by weight, more preferably 12 to 30% by weight, of at least one radically polymerizable monomer (a),
- 1 to 30% by weight, preferably 3 to 10% by weight, more preferably 5 to 10% by weight of ytterbium trifluoride particles (b) having an average particle size (number average D50 value) of 25 nm or less,
- 20 to 90% by weight, preferably 30 to 70% by weight, more preferably 40 to 65% by weight, of inorganic filler (c),
- 5 to 60% by weight, preferably 15 to 50% by weight, more preferably 15 to 40% by weight of composite filler (d) and
- 0.005 to 3.0% by weight, preferably 0.01 to 2.0% by weight, more preferably 0.1 to 1% by weight of initiator for the radical polymerization (e).

Dental materials having the following composition are particularly preferred:
- 15 to 25% by weight of radically polymerizable monomers (a),
- 5 to 10% by weight of ytterbium trifluoride particles (b),
- 45 to 55% by weight of inorganic filler (c),
- 15 to 40% by weight of composite filler (d) and
- 0.1 to 0.5% by weight of initiator for the radical polymerization (e).

Unless explicitly stated otherwise, the percentages refer to the total mass of the dental material.

The amounts given for component (b) do not include the ytterbium trifluoride contained in component (d). The dental materials according to the invention preferably contain in total, i.e. in components (b) and (d), 2 to 30% by weight, more preferably 3 to 20% by weight and most preferably 4 to 12% by weight of nanoscale ytterbium trifluoride, based on the total mass of the material.

Nanoscale fillers often have a high thickening effect, which can have a detrimental effect on the manufacturability and properties of dental materials and which limits the filler quantity and, in the case of radiopaque fillers, thus also the maximum achievable radiopacity. Although larger particles have a lower thickening effect, they have a detrimental effect on the optical properties and in particular on the depth of cure of the materials, especially in the case of ytterbium trifluoride. In accordance with the invention, it was found that a high depth of cure in combination with good radiopacity can be achieved in particular if part of the nanoscale ytterbium trifluoride used is contained in the composite filler (d), i.e. is present in agglomerated form. By this partitioning and the use of ytterbium trifluoride with the particle size according to the invention, a high depth of cure and radiopacity can be achieved while minimizing the thickening effect of the filler.

Naturally, preferred materials are those in which components (a) to (e) are selected from the preferred and particularly preferred materials defined above.

The dental materials according to the invention preferably contain a total of 30 to 95% by weight, more preferably 50 to 90% by weight and most preferably 65- to 85% by weight of fillers (components (b), (c) and (d)), based on the total mass of the dental material.

Furthermore, according to the invention, those dental materials are preferred in which the filler (c) is barium-free, which contain as initiator (e) acyl and bisacyl phosphine oxides in an amount of less than 0.03% by weight, preferably 0.01% by weight or less, and/or which contain as monomer (a-4) at least one monofunctional radically polymerizable monomer, preferably in an amount of less than 2% by weight, more preferably in an amount of 0.1 to 1.9% by weight, very particularly preferably 0.2 to 1.8% by weight and most preferably 1.3 to 1.7% by weight, based on the total mass of the dental material, dental materials having these three features simultaneously being particularly preferred.

The dental materials according to the invention are characterized by a very advantageous property profile for the restoration of damaged teeth. On the one hand, they have a high radiopacity and good mechanical properties, and on the other hand, they have excellent esthetic properties and a high depth of cure.

A high depth of cure enables large layer thicknesses to be cured with light, thus considerably simplifying the handling of the materials. The materials are particularly suitable as bulk-fill composites.

The depth of cure is determined according to DIN EN ISO 4049:2018-04 and is preferably 3 mm or more, more preferably 3.5 to 5 mm. It is particularly advantageous that these through-curing depths can be realized with the materials according to the invention with a short exposure time of only 3 seconds (at 3050±305 mW/cm$^2$). The materials according to the invention allow the fabrication even of large dental fillings with only 1 to 2 layers. This enables efficient working in the posterior region.

Furthermore, the dental materials according to the invention are also excellently suited for anterior restorations due to their esthetic properties. The fabrication of esthetically convincing dental restorations is possible with only one material, and it is not necessary to use and match several materials. The advantageous esthetic properties are largely achieved by adjusting a certain ratio of contrast value (CR value) to transmission. The dental materials according to the invention preferably have a CR value of 55 to 75, more preferably of 60 to 70 and most preferably of 62 to 68. The transmission of the colored materials is preferably between 8 and 25%, more preferably between 9 and 22% and most preferably between 10 and 18%. All data refer to the cured materials.

The CR value is the ratio of the color measurement against a white and a black background. The contrast value CR (including the L, a and b values) is determined according to BS 5612 (British Standard) using a spectral colorimeter (e.g. Minolta CM-3700d). The determination of the contrast value consists of two individual measurements. For this purpose, the test specimen to be analyzed is placed in front of a black ceramic body with a maximum reflection of 4%, and correspondingly in front of a white ceramic body with a minimum reflection of 86%, and these are then analyzed colorimetrically. When using highly transparent test pieces, reflection/absorption is mainly caused by the ceramic background, whereas reflection is caused by the test piece when an opaque material is used. The ratio of reflected light against a black background to reflected light against a white background is the measure of the contrast value, with complete transmission resulting in a contrast value of 0 and complete opacity resulting in a contrast value of 100.

The interaction of CR value and transmission results in materials with outstanding optical properties. A transmission in the range according to the invention allows ambient light to penetrate into the material and makes it to appear living. At the same time, in materials with a CR value according to the invention, the color of the surrounding tooth structure radiating into the material is refracted in such a way that the material appears to have a similar color to hard dental tissue.

The transmission is measured in the manner described in the examples on round test specimens with a diameter of 20 mm and a height of 1 mm.

Due to these properties, the materials according to the invention can completely cover the color space of natural tooth colors, which usually comprises the 16 shades of the VITA classical A1-D4® shade guide with only a few shades. In the case of the materials according to the invention, each shade covers several shades of the usual 16 shades due to the defined CR value and the defined transmission in combination with its specific shade and brightness settings. The materials integrate ideally into the natural tooth because, on the one hand, they take on the color of the surrounding hard dental tissue and, at the same time, they are colored and opaque enough to avoid a grayish impression.

A particular advantage of the dental materials according to the invention is also that they have a high gloss stability in combination with good polishability and low surface roughness due to the optimally matched components of the dental material, which has a positive effect not only on the esthetic properties but also on the properties in use.

The surface texture of a restorative material is not only important for esthetic reasons, but it also has a significant influence on plaque accumulation, discoloration and wear of the restoration. Increasing roughness is correlated with increased plaque accumulation and discoloration. Therefore, finishing and polishing is an important step in the fabrication of both direct and indirect restorations. The dental materials according to the invention yield a particularly advantageous surface roughness after polishing. The surface roughness of restorative materials changes over time of use. For example, in composite materials, tooth cleaning with a toothbrush and toothpaste causes material removal and a change in surface roughness. The materials according to the invention are characterized here by a particular resistance.

The materials according to the invention have a gloss stability (after 1 hour of brushing) of 30 GU or more, preferably from 35 to 95 GU, more preferably from 40 to 90 GU. They have a polishability of 40 GU or more, preferably from 60 to 90 GU, more preferably from 70 to 80 GU. They also have a surface roughness of 0.40 μm or less, preferably from 0.01 to 0.30 μm, more preferably from 0.02 to 0.20 μm, with materials having a surface roughness of 0.03 to 0.175 μm and more preferably from 0.04 to 0.15 μm being particularly preferred.

To determine the gloss stability of the dental materials, the material to be tested is filled into a cylindrical metal mold (d=10 mm, h=5-10 mm) (n=8 per series). The material is then exposed 3× for 30 s to light in the wavelength range of 380 to 520 nm (light power 1100 mW/cm$^2$). The cured specimens are then bonded to an SEM support and end-polymerized for 350 s with light in the wavelength range of 380 to 520 nm (light power 1200 mW/cm$^2$). After the specimens are stored dry for 24 h at 37° C., they are polished to a mirror finish with a polishing machine (Phoenix 4000, Buehler) using abrasive paper (4000 grit abrasive paper, Buehler) and polishing fluid (aluminum oxide particles, particle size 0.05 micrometer, Buehler). The test specimens prepared in this way were exposed to a one-hour circular toothbrush movement (contact force 50 g) in a toothpaste slurry (toothpaste Signal anti-caries, 250 mL toothpaste per 1 L water) by means of a toothbrush simulation device (Willytec, SD-Mechatronik, Feldkirchen-Westerham, Germany; toothbrush heads from Eco-logic, Trisa, Switzerland). After each 15 min, 30 min, 45 min and 60 min of toothbrush simulation, the surface gloss is determined with a glossmeter (Novo-curve, Rhopoint, Bexhill-on-Sea, UK). The measuring principle of the glossmeter is that a light beam hits the surface to be measured at an angle of 60° and the intensity of the reflected light is measured in the instrument and compared with a reference value. The higher the value, the higher the gloss. Gloss is measured in gloss units (GU) relative to a calibration glass (black glass plate with a value of 93.7 GU). Black foam has a value of 0 GU. The commercially available material Tetric EvoCeram (2018), for example, achieves a value of 45 GU.

The polishability of the dental materials is tested as follows: Each test specimen (n=8 per series) is polished with a polisher (OptraGloss HP single-step polisher) after standardized roughening (320 grit abrasive paper, Buehler) with a defined contact pressure of 2 N. The polishing is performed under water supply with a dental handpiece (KaVo) and a rotational speed of 10 000 rpm. Each specimen is polished for 10 s/20 s/30 s. After each polishing interval, the specimen is rinsed with water spray, dried with the air blower, and both surface gloss and surface roughness are measured. The gloss achieved by the polisher is measured in gloss units (GU, analogous to the description of gloss stability) using the gloss meter described above.

To measure the surface roughness Ra (mean surface roughness Ra in μm), the samples are illuminated with focused white light using a special optical sensor (CWL). An internal optical device, whose focal length has a strong wavelength dependence, splits the white light into different colors (corresponding to the different wavelengths). A miniaturized spectrometer detects the color of the light reflected from the sample and uses an internal calibration table to determine the vertical position on the sample surface. The xy position is measured with rotary encoders. The measurement is performed with a resolution of 10 nm in height and 1 to 2 μm lateral resolution at a maximum measurement frequency of 1000 Hz. The average roughness Ra (in μm) is the arithmetic mean of the profile ordinates. The measurement is preferably performed with the FRT MicroProf measuring instrument (FRT MicroProf, Fries Research & Technology GmbH, Bergisch Gladbach, DE).

The dental materials according to the invention have after curing a flexural strength of at least 100 MPa, preferably from 100 to 200 MPa, more preferably from 100 to 180 MPa and most preferably from 100 to 160 MPa, have at 4.0 mm depth a Vickers hardness of 80% or more compared to the surface hardness (at 0.5 mm), a transmission of 10-18%, a gloss stability of preferably from 30 to 95 GU, more preferably from 35 to 90 GU and most preferably from 40 GU to 90 GU, a polishability of preferably from 50 to 95 GU, more preferably from 60 to 90 GU and most preferably from 70 GU to 90 GU, and a surface roughness of preferably 0.20 μm or less, more preferably 0.20 to 0.01 μm and most preferably from 0.15 to 0.01 µm. They are further characterized by the fact that they can be cured in a short time, preferably in 3 to 10 s, with light in the wavelength range from 380 to 520 nm (intensity peaks at 410 and 460 nm) and an intensity of 1890 to 3355 mW/cm$^2$. This combination of properties makes them suitable for the restoration of both anterior and posterior teeth.

The dental materials according to the invention also have a high radiopacity. A high radiopacity enables clear differentiation from natural tooth substance. The radiopacity is determined according to ISO standard 4049. For this purpose, a test specimen made of the polymerized dental material together with an aluminum step wedge with a step height of 1 mm is photographed with an X-ray camera. The degree of blackening of the images is compared and the radiopacity is given in % Al; 100% radiopacity corresponds to the degree of blackening of 1 mm aluminum. The materials according to the invention preferably have an X-ray opacity of 140% to 350% Al, particularly preferably 160% to 250% Al.

The dental materials according to the invention are characterized by an advantageous property profile, i.e. they achieve values in all of the above properties which are expected of dental materials according to the current state of the art. This makes it possible to manufacture dental restorations and, in particular, dental fillings with only one material, which correspond to the current state of medical knowledge.

The materials according to the invention exhibit high stability and low stickiness are packable and can be modeled. In other words, they can be processed in a similar way to amalgam and inserted into tooth cavities, condensed and modeled into a shape that matches the remaining tooth structure. They are therefore ideally suited as dental filling materials, especially for direct and indirect anterior and posterior fillings of all classes. These properties are achieved by the choice of monomers, filler type and filler quantity according to the invention.

The term "can be modeled" is understood here to mean materials which have a viscosity of preferably 10 to 500 kPa·s, more preferably 20 to 450 kPa·s and most preferably 50 to 400 kPa·s. The viscosities described here were measured as follows: 110 mg of the material to be measured is placed on a 12 mm plate/plate measuring system of a rotational viscometer (e.g. "MCR 302" from Anton Paar). The temperature is set to 23° C. and the gap distance between the plates to 0.5 mm. The samples are not trimmed after application. The sample is tempered for 2 minutes (resting phase), then sheared at a shear rate of 0.01 s$^{-1}$ for one minute. Finally, 3 data points are measured, each with one minute of shear at the shear rate of 0.01 s$^{-1}$. The average of these data points is output as the result.

The dental materials according to the invention are primarily suitable for intraoral application by the dentist for the restoration of damaged teeth (therapeutic application), in particular as dental cements, coating or veneering materials and especially as filling composites and as so-called bulk-fill composites.

The materials according to the invention can also be used extraorally (non-therapeutically), for example in the fabrication or repair of dental restorations (non-therapeutic application). They are particularly suitable as materials for the fabrication of inlays, onlays, crowns or bridges.

EXAMPLES

Dental materials were prepared with the formulations given in the following examples and tested as described. The components were mixed with each other using a magnetic stirrer, a kneader (Linden company, machine type LPM 0.5 SP) or a centrifugal mixer (Speedmixer DAC 600.2 from Hausschild).

To determine the transmission of the materials, hardened, round test specimens (diameter: 20 mm, h=1 mm) were produced and measured colorimetrically using a spectrophotometer with standard light D65 (e.g. Spectrophotometer CM-5, Minolta). As a reference measurement for 0% transmission, the beam path is completely blocked with the "zero calibration plate" belonging to the instrument. The reference measurement for 100% transmission is performed by not inserting a specimen, thus the beam path is empty. The polymerization of the specimen is performed with an LED lamp (3 s at 3050±305 mW/cm$^2$).

The flexural strength and depth of cure were measured according to ISO 4049:2009: Dentistry—Polymer-based restorative materials. The specified value of the depth of cure (DOC) corresponds to half the measured value. From a measured value of DOC/2≥3.5 mm, a material may be referred to as bulk-fillable and a depth of cure of at least 4 mm under dental conditions is considered assured. Since the depth of cure is usually reduced by coloring, bulk-fillable materials must achieve a depth of cure DOC/2 of at least 4.5 mm or more in the uncolored form (clear paste).

The Vickers hardness was determined with a Zwick Vickers hardness tester (ZHV 0.2). In addition, the depth of cure [in mm] is given, at which the Vickers hardness of a polymerized specimen, ground down transversely to the middle, is still 80% of the surface hardness.

X-ray opacity, CR value, gloss stability, polishability and surface roughness were determined in the manner described in the description.

accelerator ethyl 4-(dimethylamino)benzoate (CAS No. 10287-53-3)

bis-GMA bisphenol-A-glycidyl methacrylate (CAS No. 1565-94-2)

TCP tricyclodecane dimethanol diacrylate (CAS No. 42594-17-2)

MA836 2-([1,1'-biphenyl]-2-oxy)ethyl methacrylate

Ge photoinitiator bis(4-methoxybenzoyl)diethylgermanium (CAS No. 1469766-31-1)

glass filler barium-free Sr-, Al- and F-containing dental glass with 6% silanization, average grain size 0.7 µm, refractive index 1.50 (Glass G018-163)

chairs regulator 2-(toluene-4-sulfonylmethyl)acrylic acid ethyl ester (MA-769)

RM3 7,7(9)9-trimethyl-4,3-dioxo-3,14-dioxa-5,12-diazohexadecan-1,16-diyl-dimethacrylate SiO$_2$/ZrO$_2$ mixed oxide spherical SiO$_2$/ZrO$_2$ mixed oxide particles, average primary particle size: 3 to 30 nm, secondary particle size: 3 to 15 µm, refractive index 1.50

SR-348C ethoxylated bisphenol A dimethacrylate (CAS No. 41637-38-1)

V380 urethane dimethacrylate with aromatic groups nYbF$_3$ nanoscale ytterbium trifluoride, mean particle size 10-24 nm (number-averaged D50 value)

V837 N-(2-methacryloyloxyethyl)carbamic acid (2-methacryloyloxyethyl)-ester (CAS No. 139096-43-8)

CC Campherquinone

Example 1

Fabrication of a Radiopaque Composite Filler with Spherical Particles

To prepare a composite filler with the composition given in Table 1, the monomers listed in the table were first mixed together and then the $SiO_2/ZrO_2$ mixed oxide was incorporated into the monomer mixture. Dispersion was carried out in a cylindrical glass by moderate stirring for 6 to 24 hours. Following this, camphorquinone and ethyl 4-(dimethylamino)benzoate (accelerator) were added and stirring continued until the initiator components dissolved. The mixture was then pumped at 20 ml/min into an atomizer nozzle operated at a pressure of 2.1 bar under nitrogen. The finely atomized droplets were polymerized using six 100 Watt LED lamps of wavelength 470 nm. The size of the cured particles was determined by laser diffraction (Microtrac X-100 particle measuring device). The particles had a spherical structure and an average particle size of 20 μm. The particle size can be controlled by adding acetone to the monomer mixture before automizing (0 to 25%). FIG. 5 shows a scanning electron micrograph of the spherical particles. The composite filler has a refractive index of 1.502.

TABLE 1

Composition of the radiopaque spherical composite filler

| Component | Proportion [wt. %] |
| --- | --- |
| V380 | 7.37 |
| RM3 | 7.83 |
| D3MA | 19.16 |
| nYbF3 | 9.85 |
| CC and accelerator | 0.41 |
| SiO2/ZrO2 mixed oxide | 55.00 |
| Additive | 0.39 |
| Total | 100 |

Example 2

Production of a Dental Material According to the Invention

To produce a dental material with the composition given in Table 2, the monomers mentioned were first mixed homogeneously under stirring, and then the ytterbium trifluoride was incorporated into part of the mixture, so that a largely transparent liquid was obtained. Subsequently, the remaining monomers and then the powdered components were added and homogeneously mixed to form a paste. The material was analyzed in the manner described above. The results are given in Table 3.

TABLE 2

Composition of the radiopaque composite paste

| Component | Proportion [wt. %] |
| --- | --- |
| Composite filler (example 1) | 24.85 |
| SiO2/ZrO2 mixed oxide | 9.94 |
| Glass filler | 38.07 |
| V380 | 4.14 |
| SR-348C | 2.83 |
| TCP | 5.51 |
| V837 | 0.56 |
| MA-836 | 1.44 |
| RM3 | 3.65 |
| Chain regulator | 0.99 |
| CC | 0.04 |
| Accelerator | 0.15 |
| Ge photoinitiator | 0.03 |
| Additive | 0.64 |
| nYbF3 | 7.17 |
| Total | 100 |

TABLE 3

Properties of the hardened dental material

| Measured parameter | Material |
| --- | --- |
| DOC/2 (mm) | 5.0 |
| Transmission (%) | 13.5 |
| Flexural strength (MPa) | 114 |
| Depth of cure at 80% Vickers hardness [mm]. | 6.2 |
| CR value | 61.7 |
| Radiopacity (% Al) | 205 |
| Gloss stability (GU) | 44 |
| Polishability (GU) | 74 |
| Surface roughness (μm) | 0.11 |

Example 3

Production of a Dental Material According to the Invention

To produce a dental material with the composition given in Table 4, the monomers mentioned were first mixed homogeneously under stirring, and then the ytterbium trifluoride was incorporated into part of the mixture, so that a largely transparent liquid was obtained. Subsequently, the remaining monomers and then the powdered components were added and homogeneously mixed to form a paste. The material was analyzed in the manner described above. The results are given in Table 5.

TABLE 4

Composition of the radiopaque composite paste

| Component | Proportion [wt. %] |
| --- | --- |
| Composite filler | 19.73 |
| SiO2/ZrO2 mixed oxide | 9.87 |
| Glass filler | 42.72 |
| V380 | 4.21 |
| SR-348C | 2.88 |
| TCP | 5.63 |
| V837 | 0.57 |
| MA-836 | 1.47 |
| RM3 | 3.71 |
| Chain regulator | 1.01 |
| CC | 0.04 |
| Accelerator | 0.15 |
| Ge photoinitiator | 0.04 |
| Additive | 0.64 |
| nYbF3 | 7.33 |
| Total | 100 |

TABLE 5

Properties of the hardened dental material

| Measured parameter | Material |
|---|---|
| DOC/2 (mm) | 5.0 |
| Transmission (%) | 13.1 |
| Flexural strength (MPa) | 124 |
| Depth of cure at 80% Vickers hardness [mm]. | 6.0 |
| CR value | 62.5 |
| Radiopacity (% Al) | 202 |
| Gloss stability (GU) | 50 |
| Polishability (GU) | 76 |
| Surface roughness (μm) | 0.10 |

Example 4

Production of a Dental Material According to the Invention

To produce a dental material with the composition shown in Table 6, the monomers mentioned were first mixed homogeneously under stirring and then the ytterbium trifluoride was incorporated into part of the mixture, so that a largely transparent liquid was obtained. Subsequently, the remaining monomers and then the powdered components were added and homogeneously mixed to form a paste. The material was analyzed in the manner described above. The results are given in Table 7.

TABLE 6

Composition of the radiopaque composite paste

| Component | Proportion [wt. %] |
|---|---|
| Composite filler | 30.00 |
| SiO2/ZrO2 mixed oxide | 10.00 |
| Glass filler | 33.30 |
| V380 | 4.08 |
| SR-348C | 2.80 |
| TCP | 5.41 |
| V837 | 0.55 |
| MA-836 | 1.42 |
| RM3 | 3.60 |
| Chain regulator | 0.97 |
| CC | 0.04 |
| Accelerator | 0.15 |
| Ge photoinitiator | 0.03 |
| Additive | 0.63 |
| nYbF3 | 7.03 |
| Total | 100 |

TABLE 7

Properties of the hardened dental material

| Measured parameter | Material |
|---|---|
| DOC/2 (mm) | 4.8 |
| Transmission (%) | 13.6 |
| Flexural strength (MPa) | 110 |
| Depth of cure at 80% Vickers hardness [mm] | 6.2 |
| CR value | 60.9 |
| Radiopacity (% Al) | 182 |
| Gloss stability (GU) | 54 |
| Polishability (GU) | 75 |
| Surface roughness (μm) | 0.105 |

Coloring of the Paste into a Color Suitable for Dark Teeth

The composite paste was adjusted to the following L,a,b,CR values by stepwise addition of the pigments Sicotrans red, Sicotrans yellow, Xerogel yellow and Sicovit black. Subsequently, the transmission and depth of cure were measured.

| L* | a* | b* | CR | Transmission | DOC/2 |
|---|---|---|---|---|---|
| 79.7 | 9.6 | 33.7 | 63.5 | 13.3% | 3.8 mm |

Figure 3:
FIG. 3 shows the human anterior tooth from FIG. 2 with a left-sided restoration with a commercially available esthetic composite material (Tetric EvoCeram, Ivoclar Vivadent AG) and a right-sided restoration with the material according to the invention from Example 4 shaded for dark tooth colors. Both restorations blend in well with the tooth and are practically undetectable.
Figure 4:
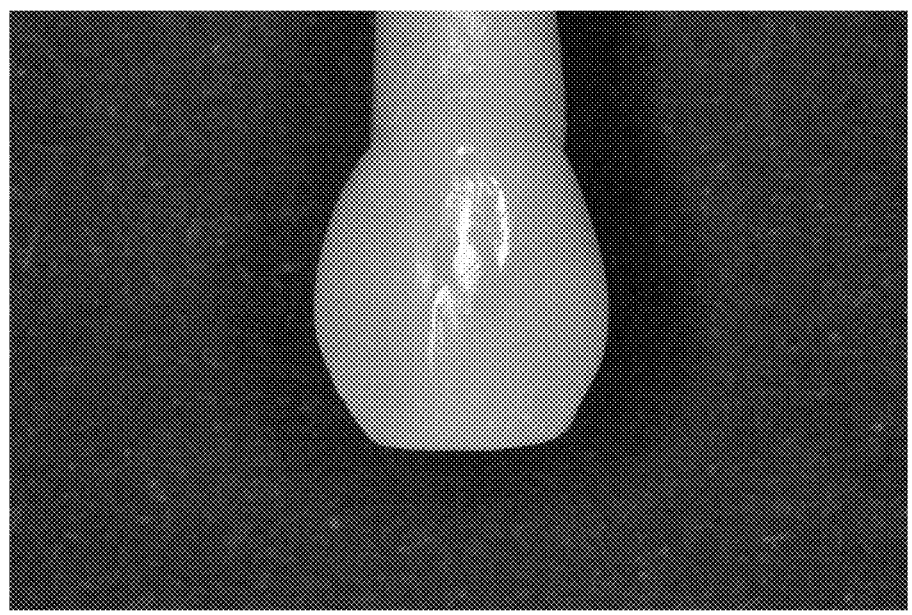
FIG. 4 shows the human anterior tooth from FIG. 2 with a left-sided restoration with a commercially available esthetic composite material (Tetric EvoCeram, Ivoclar Vivadent AG) and a right-sided restoration with the material according to the invention from Example 6 shaded for dark tooth colors. Both restorations blend in well with the tooth and are practically undetectable.

With a depth of cure of 3.8 mm, the material is a bulk-fill material according to ISO4049:2019, which according to FIG. 3 achieves comparable esthetics to a conventional esthetic 2 mm material, but has the advantage that it can be cured in layer thicknesses of 4 mm, allowing highly efficient working in the posterior teeth.

Example 5

Production of a Dental Material According to the Invention

To produce a dental material with the composition given in Table 8, the monomers mentioned were first mixed homogeneously under stirring, and then the ytterbium trifluoride was incorporated into part of the mixture, so that a largely transparent liquid was obtained. Subsequently, the remaining monomers and then the powdered components were added and homogeneously mixed to form a paste. The material was analyzed in the manner described above. The results are given in Table 9.

TABLE 8

Composition of the radiopaque composite paste

| Component | Proportion [wt. %] |
|---|---|
| Composite filler | 19.81 |
| SiO2/ZrO2 mixed oxide | 9.89 |
| Glass filler | 42.58 |
| V380 | 4.36 |
| SR-348C | 2.97 |
| TCP | 5.85 |
| V837 | 0.59 |
| MA-836 | 1.53 |
| RM3 | 3.83 |
| Chain regulator | 0.73 |
| CC | 0.04 |
| Accelerator | 0.16 |
| Ge photoinitiator | 0.04 |
| Additive | 0.63 |
| nYbF3 | 6.99 |
| Total | 100 |

TABLE 9

Properties of the hardened dental material

| Measured parameter | Material |
|---|---|
| DOC/2 (mm) | 4.6 |
| Transmission (%) | 13.6 |
| Flexural strength (MPa) | 117 |
| Depth of cure at 80% Vickers hardness [mm] | 7.0 |
| CR value | 62.8 |
| Radiopacity (%AI) | 202 |
| Gloss stability (GU) | 49 |
| Polishability (GU) | 72 |
| Surface roughness (μm) | 0.12 |

Table 9 shows that Example 5 represents an excellent compromise between esthetics (low transmission of less than 14%, high CR value above 62, good gloss stability of 49 GU, very good polishability of above 70 GU and low surface roughness) and high depth of cure of the clear paste (4.6 mm according to ISO4049; even at 7.0 mm depth a Vickers hardness of 80% based on surface hardness).

Example 6

Production of a Dental Material According to the Invention

To prepare a dental material with the composition given in Table 10, the monomers mentioned were first mixed homogeneously under stirring and then the ytterbium trifluoride was incorporated into part of the mixture to obtain a largely transparent liquid. Subsequently, the remaining monomers and then the powdered components were added and homogeneously mixed to form a paste. The material was analyzed in the manner described above. The results are given in Table 11.

TABLE 10

Composition of the radiopaque composite paste

| Component | Proportion [wt. %] |
|---|---|
| Composite filler | 20.13 |
| SiO2/ZrO2 mixed oxide | 10.07 |
| Glass filler | 41.61 |
| V380 | 4.43 |
| SR-348C | 3.02 |
| TCP | 6.20 |
| MA-836 | 1.56 |
| RM3 | 4.24 |
| Chain regulator | 0.75 |
| CC | 0.04 |
| Accelerator | 0.16 |
| Ge photoinitiator | 0.04 |
| Additive | 0.64 |
| nYbF3 | 7.11 |
| Total | 100 |

TABLE 11

Properties of the hardened dental material

| Measured parameter | Material |
|---|---|
| DOC/2 (mm) | 4.5 |
| Transmission (%) | 14.0 |
| Flexural strength (MPa) | 119 |
| Depth of cure at 80% Vickers hardness [mm] | 6.3 |
| CR value | 62.0 |
| Radiopacity (% Al) | 201 |
| Gloss stability (GU) | 44 |
| Polishability (GU) | 76 |
| Surface roughness (μm) | 0.10 |

Coloring of the Paste into a Color Suitable for Dark Teeth

The composite paste from Example 6 was adjusted to the following L,a,b,CR values by stepwise addition of the pigments Sicotrans red, Sicotrans yellow, Xerogel yellow, Real red and Sicovit black. Subsequently, the transmission and depth of cure were measured.

| L* | a* | b* | CR | Transmission | DHT/2 |
|---|---|---|---|---|---|
| 77.4 | 12.0 | 32.8 | 66.9 | 12.8% | 3.6 mm |

Figure 2:
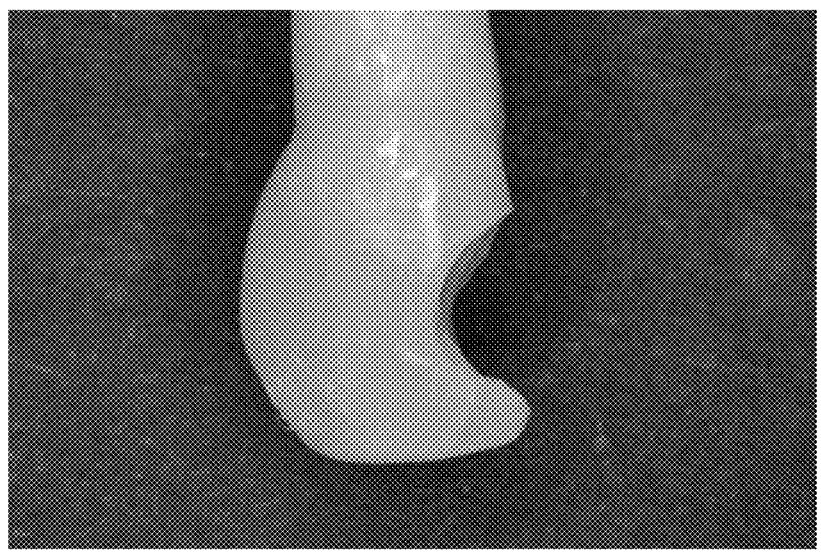
FIG. 2 shows a human anterior tooth with a left-sided restoration with a commercially available esthetic composite material (Tetric EvoCeram, Ivoclar Vivadent AG) and a right-sided large Class 3 cavity.

With a depth of cure of 3.6 mm and a hardness of 80% (based on the value at 0.5 mm depth) at a depth of 5.2 mm, the material is a bulk-fill material according to ISO4049: 2019, which achieves comparable esthetics to a conventional 2 mm esthetic material according to FIG. 2 and FIG. 3.

Example 7

Production of a Dental Material According to the Invention

To prepare a dental material with the composition given in Table 12, the monomers mentioned were first mixed homogeneously under stirring, and then the ytterbium trifluoride was incorporated into part of the mixture, so that a largely transparent liquid was obtained. Subsequently, the remaining monomers and then the powdered components were added and homogeneously mixed to form a paste. The material was analyzed in the manner described above. The results are given in Table 13.

TABLE 12

Composition of the radiopaque composite paste

| Component | Proportion [wt. %] |
|---|---|
| Composite filler | 20.00 |
| SiO2/ZrO2 mixed oxide | 10.00 |
| Glass filler | 41.90 |
| V380 | 2.62 |
| SR-348C | 4.30 |
| TCP | 5.93 |
| V837 | 0.60 |
| RM3 | 4.14 |
| Chain regulator | 0.75 |
| CC | 0.04 |
| Accelerator | 0.16 |
| Ge photoinitiator | 0.04 |
| Additive | 0.64 |
| nYbF3 | 7.09 |
| Bis-GMA | 1.80 |
| Total | 100 |

TABLE 13

Properties of the hardened dental material

| Measured parameter | Material |
|---|---|
| DOC/2 (mm) | 4.6 |
| Transmission (%) | 13.7 |
| Flexural strength (MPa) | 124 |
| CR value | 62.3 |

Example 8

Production of a Dental Material According to the Invention

To produce a dental material with the composition given in Table 14, the monomers mentioned were first mixed homogeneously under stirring and then the ytterbium trifluoride was incorporated into part of the mixture, so that a largely transparent liquid was obtained. Subsequently, the remaining monomers and then the powdered components were added and homogeneously mixed to form a paste. The material was analyzed in the manner described above. The results are given in Table 15.

TABLE 14

Composition of the radiopaque composite paste

| Component | Proportion [wt. %] |
| --- | --- |
| Composite filler | 20.00 |
| SiO2/ZrO2 mixed oxide | 10.00 |
| Glass filler | 41.90 |
| V380 | 2.62 |
| SR-348C | 2.08 |
| TCP | 5.40 |
| V837 | 0.60 |
| MA-836 | 1.43 |
| RM3 | 5.46 |
| Chain regulator | 0.75 |
| CC | 0.04 |
| Accelerator | 0.16 |
| Ge photoinitiator | 0.04 |
| Additive | 0.64 |
| nYbF3 | 7.09 |
| Bis-GMA | 1.80 |
| Total | 100 |

TABLE 15

Properties of the hardened dental material

| Measured parameter | Material |
| --- | --- |
| DOC/2 (mm) | 5.0 |
| Transmission (%) | 14.1 |
| Flexural strength (MPa) | 108 |
| CR value | 61.1 |

The invention claimed is:

1. A dental material that comprises
(a) 5 to 40% by weight of at least one radically polymerizable monomer,
(b) at least one radiopaque filler comprising 1 to 30% by weight ytterbium trifluoride particles having an average particle size of <25 nm, wherein the average particle size is the number-averaged D50 value,
(c) 20 to 90% by weight of at least one inorganic filler,
(d) 5 to 60% by weight of at least one composite filler and
(e) 0.005 to 3.0% by weight of at least one initiator for the radical polymerization,
in each case in relation to the total mass of the dental material
wherein the dental material comprises as monomer (a)
(a-1) at least one urethane (meth)acrylate,
(a-2) at least one radically polymerizable bisphenol A derivative,
(a-3) optionally at least one polycyclic aliphatic dimethacrylate,
(a-4) optionally at least one monomer which does not fall into one of the groups (a-1) to (a-3) and (a-5), and
(a-5) optionally at least one chain regulator.

2. The dental material according to claim 1, which comprises
(a-1) 20 to 80% by weight of the at least one urethane (meth)acrylate,
(a-2) 8 to 45% by weight of the at least one radically polymerizable bisphenol A derivative,
(a-3) 10 to 50% by weight of the at least one polycyclic-aliphatic dimethacrylate,
(a-4) 0 to 20% by weight of the at least one monomers which does not fall into any of groups (a-1) to (a-3) and (a-5), and
(a-5) 0 to 8% by weight of the at least one chain regulator,
in each case based on the total mass of component (a).

3. The dental material according to claim 1, which comprises as the urethane (meth)acrylate (a-1)
one or more urethane dimethacrylate monomers comprising aromatic groups,
one or more urethane di(meth)acrylates of the general formula I:

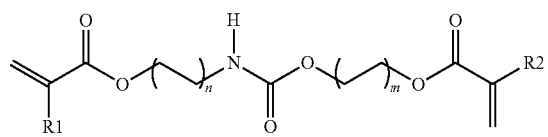

Formula I in which the variables have the following meanings:
$R^1$, $R^2$=independently of one another are each $C_1$-$C_8$-alkyl;
n, m=are each independently an integer from 1 to 2,
one or more further urethane di(meth)acrylates,
or any mixture thereof.

4. The dental material according to claim 3, which comprises as the urethane (meth)acrylate (a-1)
5 to 60% by weight of the at least one urethane dimethacrylate monomer having aromatic groups,
0 to 5% by weight of the at least one urethane di(meth)acrylate of the formula I, and
10 to 70% by weight of the one or more further urethane dimethacrylate,
in each case based on the total mass of the monomer component (a).

5. The dental material according to claim 1, which comprises
as the at least one radically polymerizable bisphenol A derivative (a-2): 2,2-bis[4-(2-hydroxy-3-methacryloyloxypropyl)phenyl]propane (bis-GMA), and/or
as the at least one polycyclic aliphatic dimethacrylate (a-3): a tricyclodecanedimethanol dimethacrylate, and/or
as the at least one monomer (a-4) which does not fall into any of the groups (a-1) to (a-3) and (a-5): at least one (meth) acrylamide, bis(meth) acrylamide, monofunctional methacrylate, polyfunctional methacrylate or mixture thereof.

6. The dental material according to claim 5, which comprises
8 to 45% by weight of the at least one bisphenol A derivative (a-2), and/or
10 to 50% by weight of the at least one polycyclic aliphatic dimethacrylate (a-3), and/or
not more than 20% by weight of the at least one monomer (a-4),
in each case based on the total mass of the monomer component (a).

7. The dental material according to claim 1, comprising as chain regulator (a-5): at least one arylsulfonylalkyl acrylic acid alkyl ester, 2-(toluene-4-sulfonylmethyl) acrylic acid ethyl ester (TSMEA), 2-(toluene-4-sulfonylmethyl) acrylic acid 2-(2-ethoxy-ethoxy)ethyl ester, 2-(toluene-4-sulfonylmethyl)-acrylic acid, 2-(toluene-4-sulfonylmethyl)-acrylic acid tert-butyl ester, 3-(trimethoxysilyl) propyl-2-(tosylmethyl) acrylate, 3-(triethoxysilyl) propyl 2-(tosylmethyl) acrylate, 3-(triethoxysilyl) propyl 2-(tosylmethyl) acryl amide, 2-(methylsulfonyl)ethyl methacrylate, 2-(methylsulfonyl)-ethyl methacrylate, 3-(methylsulfonyl)-propyl methacrylate, triethylene glycol-bis[2-(toluene-4-sulfonyl-methyl) acrylate], 2-(toluene-4-sulfonylmethyl) acrylic acid (2-methacryloyloxyethyl) ester, 2-(toluene-4-sulfonylmethyl) acrylic acid (6-methacryloyloxyhexyl) ester, 2-(toluene-4-sulfonylmethyl) acrylic acid (10-methacryloyloxydecyl) ester, 2-(toluene-4-sulfonylmethyl) acrylic acid (2-hydroxy-3-methacryloyloxypropyl) ester, 2-(toluene-4-sulfonylmethyl) acrylic acid (8-methacryloyloxy-3,6-dioxaoctyl) ester,
in an amount of 0 to 8% by weight, based on the mass of monomer component (a).

8. The dental material according to claim 1, in which the monomer component (a) has a refractive index of from 1.495 to 1.520, wherein the refractive index of the monomer mixture is adjusted such that before curing it corresponds to the refractive index of filler (c) or is at most 0.03 higher than the refractive index of filler (c).

9. The dental material according to claim 1, which comprises as component (b): ytterbium trifluoride particles with an average particle size of 10 to 24 nm, wherein the average particle size is the number-averaged D50 value, and/or
comprises as inorganic filler (c): at least one glass powder, with an average particle size of 0.1 to 1.5 μm, at least one $SiO_2/ZrO_2$ mixed oxide, with an average primary particle size of 2 to 100 nm and an average secondary particle size of 0.5 to 30 μm, or a mixture thereof, wherein the average particle sizes of the inorganic filler (c) are in all cases the volume-averaged D50 values.

10. The dental material according to claim 1, which comprises as component (d) a particulate composite material prepared by polymerization of the following composition:
8 to 50% by weight of radically polymerizable monomer,
1 to 20% by weight ytterbium trifluoride particles with an average particle size of <25 nm, wherein the average particle size is the number-averaged D50 value,
40 to 90% by weight of further inorganic fillers and
0.01 to 2% by weight initiator for the radical polymerization,
in each case based on the total mass of the composite filler.

11. The dental material according to claim 1, which comprises
10 to 35% by weight of the at least one radically polymerizable monomer (a),
3 to 10% by weight of the ytterbium trifluoride particles (b) having an average particle size of <25 nm, wherein the average particle size is the number-averaged D50 value,
30 to 70% by weight of the inorganic filler (c),
15 to 50 wt. % composite filler (d) and
0.01 to 2.0% by weight of the initiator for the radical polymerization (e),
in each case in relation to the total mass of the dental material.

12. The dental material according to claim 1, which has the following composition:
(a) 5 to 40% by weight of the at least one radically polymerizable monomer,
(b) 1 to 30% by weight of the ytterbium trifluoride with an average particle size of <25 nm as X-ray opaque filler, wherein the average particle size is the number-averaged D50 value,
(c) 20 to 90% by weight of the at least one inorganic filler,
(d) 5 to 60% by weight of the at least one composite filler and
(e) 0.01 to 3.0% by weight of the at least one initiator for the radical polymerization, in each case in relation to the total mass of the dental material,
wherein the dental material comprises as the radically polymerizable monomer (a): a mixture of
(a-1) 20 to 80% by weight of urethane dimethacrylates comprising
5 to 60% by weight tetramethylxylylene diurethane dimethacrylate (V380),
5 to 60% by weight of other urethane methacrylates,
(a-2) 5 to 30% by weight of at least one radically polymerizable bisphenol A dimethacrylate,
(a-3) 10 to 50% by weight of at least one polycyclic aliphatic dimethacrylate, and
(a-4) 0 to 20% by weight of at least one monomer which does not fall into any of the groups (a-1) to (a-3) and (a-5), and
(a-5) 0 up to 8% by weight of at least one chain regulator,
in each case based on the total mass of component (a), the monomer component (a) having a refractive index of from 1.495 to 1.520,
as the inorganic filler (c):
glass powder having a refractive index in the range from 1.49 to 1.52 and an average particle size of from 0.4 to 0.9 μm, optionally
one or more $SiO_2/ZrO_2$ mixed oxides having a refractive index in a range 1.490 to 1.510, having an average primary particle size of 2 to 100 nm and an average secondary particle size of 0.5 to 30 μm, or a mixture thereof, wherein the average particle sizes of the inorganic filler (c) are in all cases the averaged D50 values,
and
as the composite filler (d): a filler having an average particle size of from 5 to 100 μm, wherein the average particle size is the volume-averaged D50 value, which is prepared by polymerizing a composition comprising
8 to 50% by weight of radically polymerizable monomer selected from glycerol dimethacrylate, alkylene dimethacrylates 1,10-decanedioldimethacrylate ($D_3MA$), triethylene glycol dimethacrylate (TEGDMA), urethanedimethacrylates, 1,6-bis[2-methacryloyloxyethoxy-carbonylamino]-2,2,4-trimethylhexane (RM3), N-(2-methacryloyloxyethyl) carbamic acid (2-methacryloyloxyethyl) ester (V837), tetramethyl-xylylene diurethane-di(meth)acrylate (V380) and mixtures thereof,
8 to 13% by weight ytterbium trifluoride particles with an average particle size of <25 nm, wherein the average particle size is the number-averaged D50 value,
40 to 90% by weight of further inorganic filler and
0.01 to 2% by weight of initiator for the radical polymerization,
in each case based on the total mass of the composite filler,
and
wherein the refractive index of the monomer component (a) is equal to or at most 0.03 greater than the refractive index of the filler (c), and wherein the refractive index of the monomer component (a) is equal to or at most 0.025 greater than the refractive index of the composite filler (d).

13. The dental material according to claim 1, comprising
(a) 12 to 30% by weight of the at least one radically polymerizable monomer, (b) 3 to 10% by weight of the ytterbium trifluoride having an average particle size of 10 to 24 nm as X-ray opaque filler, wherein the average particle size is the number-averaged D50 value,
(c) 30 to 70% by weight of the at least one inorganic filler,
(d) 15 to 50% by weight of the at least one composite filler and
(e) 0.01 to 2.0% by weight of the at least one photoinitiator for the radical polymerization,
in each case in relation to the mass of the dental material, wherein the dental material comprises as the radically polymerizable monomer (a): a mixture of
(a-1) 20 to 80% by weight of urethane dimethacrylates comprising
  5 to 60% by weight of tetramethylxylylene diurethane dimethacrylate (V380),
  and
  10 to 70% by weight of 1,6-bis-[2-methacryloyloxy-ethoxycarbonylamino]-2,2,4-trimethylhexane (RM3),
(a-2) 8 to 45% by weight of bisphenol A dimethacrylate 2-[4-(2-meth acryl oyloxyethoxyethoxy)phenyl]-2-[4-(2-methacryloyloxyethoxy)]propane) (SR-348c), 2,2-bis[4-(2-hydroxy-3-methacryloyloxypropyl)phenyl]propane (Bis-GMA), or a mixture thereof
(a-3) 15 to 40% by weight of bis-(3-methacryloyloxymethyl)tricyclo-[5.2.1.0$^{2,6}$]decane (TCP), and
(a-4) 4 to 10% by weight of at least one monomers which does not fall into any of the groups (a-1) to (a-3) and (a-5), and
(a-5) 0.5 to 7% by weight of at least one chain regulator,
in each case based on the total mass of component (a), as the inorganic filler (c):
barium-free strontium glass powder with a refractive index in the range from 1.49 to 1.51 and an average particle size of 0.4 to 0.9 μm and/or
one or more $SiO_2/ZrO_2$ mixed oxides with a refractive index in a range of 1.490 to 1.510, with an average primary particle size of 2 to 100 nm, and an average secondary particle size of 0.5 to 30 μm, or a mixture thereof, wherein the average particle sizes of the inorganic filler (c) are in all cases the averaged D50 values, and as the composite filler (d): a filler having an average particle size of from 5 to 100 μm, wherein the average particle size is the volume-averaged D50 value, which is prepared by polymerizing a composition comprising
  18 to 50% by weight radically polymerizable monomer selected from glycerol dimethacrylate, 1,10-decanedioldimethacrylate (D3MA), triethylene glycol dimethacrylate (TEGDMA), 1,6-bis-[2-methacryloyloxyethoxycarbonylamino]-2,2,4-trimethylhexane (RM3), N-(2-methacryloyloxyethyl) carbamic acid (2-methacryloyloxyethyl) ester (V837), tetramethyl-xylylene diurethane di(meth)acrylate (V380), and mixtures thereof,
  8 to 13% by weight of ytterbium trifluoride particles having an average particle size of 10 to 24 nm, wherein the average particle size is the number-averaged D50 value,
  40 to 90% by weight of strontium glass powder and/or $SiO_2/ZrO_2$ mixed oxide as further inorganic filler and
  0.01 to 2% by weight of initiator for the radical polymerization,
in each case based on the total mass of the composite filler.

14. The dental material according to claim 1, which comprises
  15 to 25% by weight of the at least one radically polymerizable monomer (a),
  5 to 10% by weight of the ytterbium trifluoride particles (b)
  40 to 55% by weight of the inorganic filler (c),
  15 to 40% of the composite filler (d) and
  0.1 to 0.5% by weight of the initiator for the radical polymerization (e),
in each case in relation to the total mass of the dental material.

15. The dental material according to claim 1, for therapeutic application as dental cement, coating, veneering material, or bulk-fill composite.

16. A method of using the dental material according to claim 1 for non-therapeutic use comprising manufacturing inlays, onlays, crowns and bridges using the dental material.

* * * * *